(12) United States Patent
Nieh et al.

(10) Patent No.: US 11,760,966 B2
(45) Date of Patent: Sep. 19, 2023

(54) MULTIGEL TUMOR-ON-A-CHIP SYSTEM

(71) Applicant: University of Connecticut, Farmington, CT (US)

(72) Inventors: Mu-Ping Nieh, Mansfield, CT (US); Armin Tahmasbi Rad, Manchester, CT (US); Reza Amin, Farmington, CT (US); Leila Daneshmandi, Manchester, CT (US)

(73) Assignee: University of Connecticut, Farmington, CT (US)

( * ) Notice: Subject to any disclaimer, the term of this patent is extended or adjusted under 35 U.S.C. 154(b) by 506 days.

(21) Appl. No.: 16/899,676

(22) Filed: Jun. 12, 2020

(65) Prior Publication Data

US 2020/0392440 A1     Dec. 17, 2020

Related U.S. Application Data

(60) Provisional application No. 62/861,456, filed on Jun. 14, 2019.

(51) Int. Cl.
| | |
|---|---|
| *C12M 3/06* | (2006.01) |
| *C12N 5/00* | (2006.01) |
| *G01N 33/50* | (2006.01) |
| *C12M 1/34* | (2006.01) |
| *C12M 1/12* | (2006.01) |

(52) U.S. Cl.
CPC ............ *C12M 23/16* (2013.01); *C12M 25/16* (2013.01); *C12M 41/46* (2013.01); *C12N 5/0012* (2013.01); *G01N 33/5008* (2013.01)

(58) Field of Classification Search
CPC ...... C12M 23/16; C12M 25/16; C12M 41/46; C12N 5/0012; G01N 33/5008; B01L 3/5027
See application file for complete search history.

(56) References Cited

U.S. PATENT DOCUMENTS

| | | | |
|---|---|---|---|
| 8,748,180 | B2 | 6/2014 | Shuler et al. |
| 9,034,571 | B2 | 5/2015 | Berry et al. |
| 9,121,847 | B2 | 9/2015 | Kamm et al. |
| 9,637,715 | B2 | 5/2017 | Hung et al. |
| 9,879,308 | B2 | 1/2018 | Holton et al. |
| 10,144,945 | B2 | 12/2018 | Wang et al. |
| 2003/0082795 | A1 | 5/2003 | Shuler et al. |
| 2005/0260745 | A1 | 11/2005 | Domansky et al. |

(Continued)

FOREIGN PATENT DOCUMENTS

| | | |
|---|---|---|
| JP | 5881031 B2 | 3/2016 |
| KR | 101038484 B1 | 6/2011 |
| WO | 2018178654 A1 | 10/2018 |

OTHER PUBLICATIONS

Goy et al., "Microfluidics and Hydrogel: A powerful combination," Reac. Funct. Polym, 2019, vol. 145, 104314.

(Continued)

*Primary Examiner* — Brian J. Sines
(74) *Attorney, Agent, or Firm* — Michael Best & Friedrich LLP

(57) ABSTRACT

Described herein are apparata and methods for growing cells in a manner that mimics the native three-dimensional environment. Cell cultures grown in the apparatus can be screened for inhibition by specific chemotherapeutics or other drugs.

10 Claims, 27 Drawing Sheets

(56) References Cited

U.S. PATENT DOCUMENTS

| | | | |
|---|---|---|---|
| 2006/0154361 A1* | 7/2006 | Wikswo | C12M 23/16 |
| | | | 435/297.5 |
| 2009/0018033 A1 | 1/2009 | Morgan et al. | |
| 2011/0081664 A1 | 4/2011 | Forbes et al. | |
| 2011/0129850 A1 | 6/2011 | Tseng et al. | |
| 2011/0183312 A1 | 7/2011 | Huang et al. | |
| 2012/0135452 A1 | 5/2012 | Shuler et al. | |
| 2014/0273223 A1 | 9/2014 | Cho et al. | |
| 2018/0085750 A1 | 3/2018 | Varghese et al. | |
| 2018/0141047 A1 | 5/2018 | Ponomarenko | |
| 2018/0179481 A1 | 6/2018 | Fujimoto et al. | |
| 2018/0272346 A1* | 9/2018 | Griffith | C12M 25/04 |
| 2018/0280971 A1 | 10/2018 | Borenstein et al. | |
| 2018/0326417 A1* | 11/2018 | Wikswo | C12M 23/34 |
| 2019/0032021 A1 | 1/2019 | Ingber et al. | |
| 2019/0106665 A1 | 4/2019 | Ingber et al. | |
| 2019/0112666 A1 | 4/2019 | Barbie et al. | |
| 2020/0017811 A1 | 1/2020 | Apfel | |

OTHER PUBLICATIONS

International Search Report and Written Opinion for Application No. PCT/US2020/037370 dated Nov. 19, 2020 (18 pages).

Beckwith et al., "Monolithic, 3D-Printed Microfluidic Platform for Recapitulation of Dynamic Tumor Microenvironments," Journal of Microelectromechanical Systems, Dec. 2018, 27(6):1009-1022.

Chung et al., "Microfluidic Platforms for Studies of Angiogenesis, Cell Migration, and Cell-Cell Interactions," Annals of Biomedical Engineering, Jan. 2010, 38:1164-1177.

Coppeta et al., "A portable and reconfigurable multi-organ platform for drug development with onboard microfluidic flow control," Lab on a Chip, 2017, 17:134-144.

Goliwas et al., "Methods to Evaluate Cell Growth, Viability, and Response to Treatment in a Tissue Engineered Breast Cancer Model," Scientific Reports, Oct. 2017, 7:14167.

Holton et al., "Microfluidic Biopsy Trapping Device for the Real-Time Monitoring of Tumor Microenvironment," PLoS One, Jan. 2017, 12(1):e0169797.

Khademhosseini et al., "Micromolding of photocrosslinkable hyaluronic acid for cell encapsulation and entrapment," J. of Biomedical Materials Research, Jun. 2006, 79A(3):522-532.

Lee et al., "Diffusion-mediated in situalginate encapsulation of cell spheroids using microscale concave well and nanoporous membrane," Lab Chip, Feb. 2011, 11:1168-1173.

Mannino et al., "3D microvascular model recapitulates the diffuse large B-cell lymphoma tumor microenvironment in vitro," Lab on a Chip, 2017, 17:407-414.

Mcguigan et al., "Cell Encapsulation in Sub-mm Sized Gel Modules Using Replica Molding," PLoS One, May 2008, 3(5):e2258.

Moore et al., "A multiplexed microfluidic system for evaluation of dynamics of immune-tumor interactions," Lab on a Chip, 2018, 18:1844-1858.

Pasturel et al., "Tailoring 3D cell culture templates with common hydrogels," bioRxiv, Aug. 2019, 370882.

Schukur et al., "Directed Differentiation of Size-Controlled Embryoid Bodies Towards Endothelial and Cardiac Lineages in RGD-Modified Poly(Ethylene Glycol) Hydrogels," Advanced Healthcare Materials, Jan. 2013, 2(1)195-205.

Xu et al., "Application of a microfluidic chip-based 3D co-culture to test drug sensitivity for individualized treatment of lung cancer," Biomaterials, May 2013, 34(16)4109-4117.

* cited by examiner

MULTIGEL TUMOR-ON-A-CHIP SYSTEM

CROSS-REFERENCE TO RELATED APPLICATIONS

This application claims priority to U.S. Provisional Patent Application No. 62/861,456, filed on Jun. 14, 2019, the contents of which are incorporated by reference herein in its entirety.

TECHNICAL FIELD

Described herein are apparata and methods for growing cells in a manner that mimics the native three-dimensional environment. Cell cultures grown in the apparatus can be screened for inhibition by specific chemotherapeutics or other drugs.

BACKGROUND

The primary clinical strategy for cancer treatment in advanced stages is chemotherapy. Drugs are selected by the primary oncologists often by their success rates in previous patients. If the first line of treatment fails, alternative drugs may be administered in multiple rounds of chemotherapy. The reason for these failures has been attributed to the genetic variability in between patients, and the inherent heterogeneous nature of cancer, and its innate ability to acquire resistance against certain drugs. For example, 80% of advanced ovarian cancer patients encounter failure in their first cycle of chemotherapy. Therefore, a device that could screen the efficiency of chemotherapeutic drugs against a patient's cancer cells prior to starting treatment, would greatly improve the success rates and would diminish these complications.

There are a few strategies proposed for personalized cancer therapy based on genetic testing and individualized cancer cell screening. However, these methods are limited in that they do not evaluate the response of the patient's cells to the candidate drug in an environment similar to that of the human body. By not providing the natural 3D microenvironment of the cancer cells ex vivo and by not assessing cellular function and performance in these settings, the accuracy of the results is severely restricted.

Previous groups have developed microfluidic devices that permit growth of patient derived tumor cell spheroids. See e.g., WO 2016112172 A1. These devices do not permit tracking the tumor growth and do not replicate the 3D architecture of the surrounding tissue.

What is needed are apparata and methods for culturing solid tumors or tumor cells in a three-dimensional environment mimicking the natural tissues of an organism that can be used to evaluate the efficacy of therapeutics and screen for novel therapeutics.

SUMMARY

One embodiment described herein is a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel. In one aspect the device comprises a cell culture medium inlet and outlet in fluid communication with each other via a cell culture medium channel, and one or more cell encapsulated hydrogel inputs in fluid communication with a plurality of cell encapsulated microgel delivery channels and the cell growing chamber. In another aspect, the plurality of layers comprises hydrophilic polymer sheets comprising one or more of polyacrylic acid, polymethylmethacrylate, polycarbonate, polyester, nylon, polyvinyl chloride, polyethylene, polypropylene, polyethylene terephthalate glycol, polybutylene adipate terephthalate, ethylene tetrafluoroethylene, fluorinated ethylene propylene, perfluoroalkoxy alkane, polylactic acid, polycaprolactone, polyoxymethylene, cellulose, co-polymers thereof, or combinations thereof. In another aspect, the plurality of uncured spaces comprises one or more of cylindrical, spherical, cubic, or other shaped wells. In another aspect, the first and second cured hydrogels are cured by different mechanisms. In another aspect, the curing of the second hydrogel does not damage the tumor cells. In another aspect, the first cured hydrogel is UV/light-cured. In another aspect, the first cured hydrogel comprises a 4-arm polyethylene glycol acrylate, gelatin, fibrin, agarose, chitosan, solubilized basement membrane preparation (Matrigel®), or a combination thereof. In another aspect, the second cured hydrogel is thermally cured. In another aspect, the second cured hydrogel comprises one or more of a solubilized basement membrane preparation (Matrigel®), a gelatinous protein mixture, gelatin methacrylamide (GelMA), or combination thereof. In another aspect, the tumor cells are from a subject biopsy, human cell line, or animal cell line. In another aspect, the device has the structure of any one of the drawings or descriptions described herein.

Another embodiment described herein is a method for monitoring cell growth and viability, the method comprising: isolating cells from a subject or a human or animal cell line; encapsulating the cells in a curable hydrogel; inserting the encapsulated cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of cells encapsulated in a second cured hydrogel; incubating the encapsulated cells in the microfluidic device under conditions favorable for cell growth for a period of time; and analyzing the encapsulated cells in the microfluidic device. In one aspect, the method further comprises contacting the encapsulated cells with fluorescently labeled species comprising one or more of small molecules, nanoparticles, nanoparticles comprising nanodiscs, nanovesicles, or liposomes; and analyzing the nanoparticles. In another aspect, the analyzing comprises light microscopy, fluorescence microscopy, other imaging methods, flow cytometry, immunohistochemistry, immunofluorescence, histological analysis, in situ hybridization techniques, apoptotic assays, ELISA, radioimmunoassays, proteomic approaches (targeted or shotgun-based), or PCR-based assays. In another aspect, the method further comprises determining viability of the encapsulated cells. In one aspect, the method further comprises contacting the encapsulated cells with one or more drugs for a period of time; incubating the encapsulated cells for a period of time; and analyzing changes or the reduction in viability of the contacted encapsulated cells after the incubation period. In another aspect, the drugs comprise chemotherapeutic drugs or agents, cytotoxins, antibiotics, anti-viral agents, immunomodulatory agents, or anti-inflammatory agents. In another aspect, the drugs comprise anti-cancer chemotherapeutics. In another aspect, the contacting the encapsulated cells with one or more drugs comprises a sequential or stepwise administration of the one or more drugs. In another aspect, the method further comprises, initiating, maintaining, or modifying therapeutic treatment or dosage thereof of a subject from whom the cells were obtained based on the analysis of the encapsulated cells.

Another embodiment described herein is a method for evaluating the efficacy of a chemotherapeutic treatment on a subject's tumor, the method comprising: isolating tumor cells from a subject's tumor; encapsulating the tumor cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; evaluating the efficacy of the chemotherapeutic drug on the encapsulated tumor cells; and initiating, maintaining, or modifying chemotherapeutic treatment and dosage thereof of the subject from whom the tumor cells were isolated. In one aspect, the contacting comprises a single, sequential, or stepwise administration of one or more chemotherapeutic drugs. In another aspect, the chemotherapeutic drug comprises one or more of alkylating agents, antimetabolites, anti-tumor antibiotics, topoisomerase inhibitors, mitotic inhibitors, platinum-based agents, or biologics.

Another embodiment described herein is a method for screening the effectiveness of a chemotherapeutic drug on a tumor cell, the method comprising: obtaining tumor cells from one or more subjects or established tumor cell lines; encapsulating the tumor cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; and evaluating the effectiveness of the chemotherapeutic drug on diminishing the viability of the encapsulated tumor cells. In one aspect, the contacting comprises a single, sequential, or stepwise administration of one or more chemotherapeutic drugs.

Another embodiment described herein is a means for screening the effectiveness of a chemotherapeutic drug on a tumor cell, comprising: obtaining tumor cells from one or more subjects or established tumor cell lines; encapsulating the tumor cells in a curable hydrogel and inserting the cells in a multi-layer, multi-gel microfluidic device; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; and evaluating the effectiveness of the chemotherapeutic drug on diminishing the viability of the encapsulated tumor cells.

Another embodiment described herein is the use of a multi-layer, multi-gel microfluidic device for screening the effectiveness of a chemotherapeutic drug on a tumor cell, comprising: obtaining tumor cells from one or more subjects or established tumor cell lines; encapsulating the tumor cells in a curable hydrogel and inserting the cells in a multi-layer, multi-gel microfluidic device; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; and evaluating the effectiveness of the chemotherapeutic drug on diminishing the viability of the encapsulated tumor cells.

Another embodiment described herein is a method for isolation and preparation of cells from a subject for inclusion in a multi-layer, multi-gel microfluidic device, the method comprising: obtaining tissue or a tumor from a subject's biopsy sample or surgical excision; placing the tissue or tumor in a medium for transport or temporary storage; removing the media; macerating the tissue in fresh media; pelleting the cells, removing the supernatant, and resuspending the cell pellet; incubating the resuspended cell pellet with enzymes for a period of time; pelleting the cells and removing the supernatant; optionally, resuspending the cell pellet, straining the cells with a cell strainer, and re-pelleting the cells; resuspending the cell pellet with warm media; counting the cells and diluting to a specific concentration; encapsulating the diluted cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; and incubating the encapsulated tumor cells in the microfluidic device under conditions favorable for tumor cell growth for a period of time.

Another embodiment described herein is a method of manufacturing a multi-layer, multi-gel microfluidic device, comprising: fabricating a plurality of layers, the layers defining a cell growing chamber in fluid communication with a culture medium channel, a cell culture medium inlet and outlet in fluid communication with each other via the cell culture medium channel, and one or more cell encapsulated hydrogel inputs in fluid communication with a plurality of cell encapsulated microgel delivery channels and the cell growing chamber, depositing a first hydrogel in the cell growing chamber and curing in manner to provide a cured first hydrogel with a plurality of uncured spaces comprising one or more cylindrical wells, depositing a population of cells in a second hydrogel into the uncured spaces and curing the second hydrogel to provide a population of cells encapsulated in a second cured hydrogel, assembling the multilayer device, and assembling connectors and tubes. In one aspect, the fabrication is by one or more of laser cutting, die cutting, milling, press cutting, layer-by-layer fabrication, 3D printing, lithography, or combinations thereof.

Another embodiment described herein is a multi-layer, multi-gel microfluidic device manufactured as described herein.

Another embodiment described herein is a kit comprising: one or more multi-layer, multi-gel microfluidic devices, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; a UV-curable hydrogel; a thermosettable hydrogel; tubing, syringes, and containers for preparation of the hydrogels, and introducing media or drugs into the device; optionally, culture media or chemotherapeutics drugs; sealed packaging; and instructions or directions for use.

DESCRIPTION OF THE DRAWINGS

The patent or application contains at least one drawing executed in color. Copies of this patent application publication or patent with color drawing(s) will be provided by the Office upon request and payment of the necessary fee.

FIG. 13 shows concentration n vs. time plots for the flow chambers and free flow domains of Geometry 1.

FIG. 14A, t=0; FIG. 14B, t=2 sec; FIG. 14C, t=4 sec; FIG. 14D, t=6 sec. Units for concentrations are in mole/m$^3$ and times values are in seconds.

FIG. 15A, t=0; FIG. 15B, t=2 sec; FIG. 15C, t=4 sec; FIG. 15D, t=6 sec. Units for concentrations are in mole/m$^3$ and times values are in seconds.

FIG. 16A, t=0; FIG. 16B, t=2 sec; FIG. 16C, t=4 sec; FIG. 16D, t=6 sec. Units for concentrations are in mole/m$^3$ and times values are in seconds.

FIG. 17A, t=0; FIG. 17B, t=2 sec; FIG. 17C, t=4 sec; FIG. 17D, t=6 sec. Units for concentrations are in mole/m$^3$ and times values are in seconds.

FIG. 18A, t=0; FIG. 18B, t=2 sec; FIG. 18C, t=4 sec; FIG. 18D, t=6 sec. Units for concentrations are in mole/m$^3$ and times values are in seconds.

FIG. 25A shows the quantification of fluorescently labeled discs and vesicles penetration into the tumor tissue during the first hour. FIG. 25B shows micrographs were taken at the end of 1 hour. Scale bar is 100 μm.

FIG. 26A shows the fluorescence of tumor tissues 1 hour after the NP-containing fluid started to flow in the cases of labeled FA-nanodiscs and FA-vesicles. FIG. 26B shows micrographs after 1 hour. Scale bar is 100 µm.

DETAILED DESCRIPTION

Figure 1A:
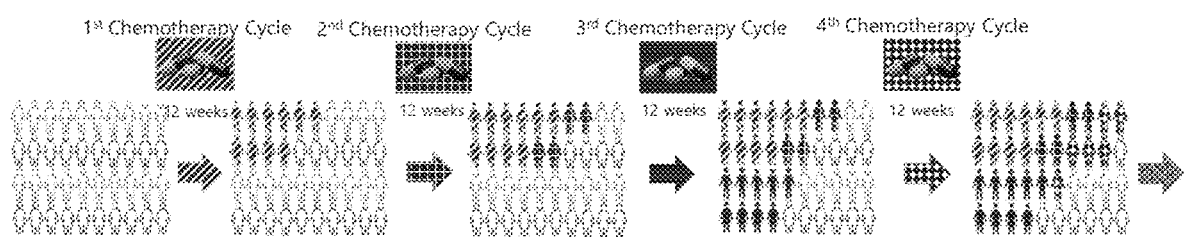
FIG. 1A shows a schematic overview of the current clinical procedure.

As used herein, the terms "comprise(s)," "include(s)," "having," "has," "can," "contain(s)," and variants thereof, to be open-ended transitional phrases, terms, or words that do not preclude the possibility of additional acts or structures. The present disclosure also contemplates other embodiments "comprising," "consisting of," and "consisting essentially of," the embodiments or elements presented herein, whether explicitly set forth or not.

As used herein, the terms "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

For the recitation of numeric ranges herein, each end point and intervening numbers within the range are explicitly contemplated with the same degree of precision. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "about" as used herein refers to any values, including both integers and fractional components that are within a variation of up to ±10% of the value modified by the term "about."

As used herein the terms "device," "system," "microfluidic chips," "multi-layer, multi-gel microfluidic device," or "tumor-on-a-chip" are synonymous and refer to the multi-layer, multi-gel microfluidic devices described herein that can be used to grow and cultivate cells or particularly tumor cells, thus forming a "tumor-on-a-chip" system.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

As used herein, the terms "control," "reference level," and "reference" are used interchangeably and refer to a predetermined value or range, which is employed as a benchmark against which to assess the measured result.

The term "dose" as used herein denotes any form of the active ingredient formulation or composition that contains an amount sufficient to produce a therapeutic effect with at least a single administration. "Formulation" and "composition" are used interchangeably herein.

The term "dosage" as used herein refers to the administering of a specific amount, number, and frequency of doses over a specified period of time, typically 1 day.

As used herein, the terms "effective amount," "therapeutically effective amount," or "therapeutically effective rate (s)" refers to a substantially non-toxic, but sufficient amount or delivery rates of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. It is understood that various biological factors may affect the ability of an agent to perform its intended task. Therefore, an "effective amount," "therapeutically effective amount," or "therapeutically effective rate(s)" may be dependent in some instances on such biological factors. For example, the precise determination of what would be considered an effective dose may be based on factors individual to each patient, including, but not limited to, the patient's age, size, type or extent of disease, stage of the disease, route of administration, the type or extent of supplemental therapy used, ongoing disease process and type of treatment desired (e.g., aggressive vs. conventional treatment). Further, while the achievement of therapeutic effects may be measured by a physician or a qualified medical practitioner using evaluations known in the art, it is recognized that individual variation and response to treatments may make the achievement of therapeutic effects a subjective decision. An appropriate "effective" amount in any individual case may be determined using techniques, such as a dose escalation study. The dose could be administered in one or more administrations. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In one embodiment, at least one ingredient is an active agent or otherwise has properties that exert physiologic activity when administered to a subject.

As used herein, the terms "inhibit," "inhibition," or "inhibiting" refer to the reduction or suppression of a given condition, symptom, or disorder, or disease, or a significant decrease in the baseline activity of a biological activity or process.

As used herein, a subject is "in need of" a treatment if such subject would benefit biologically, medically, or in quality of life from such treatment.

As used herein, the term "preventing" refers to a reduction in the frequency of, or delay in the onset of, symptoms of the condition or disease.

As used herein, the term "prophylaxis" refers to preventing or reducing the progression of a disorder, either to a statistically significant degree or to a degree detectable to one having ordinary skill in the art.

As used herein, the terms "sample" or "test sample" refers any sample in which the presence and/or level of a target is to be detected or determined or any sample treated with the compositions as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the terms "subject," "study participant," "participant," and "patient" interchangeably refer to any vertebrate, including, but not limited to, a mammal that wants or is in need of the herein described compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male or female. In some embodiments, the subject has a specific genetic marker. The subject may be undergoing other forms of treatment. In one aspect, the subject is one or more cells or tumors from a subject.

As used herein, the term "substantially" means to a great or significant extent, but not completely.

As used herein, the terms "treat", "treating," or "treatment" of any disease or disorder refer In an embodiment, to ameliorating the disease or disorder (i.e., slowing or arresting or reducing the development of the disease or at least one of the clinical symptoms thereof). In an embodiment, "treat," "treating," or "treatment" refers to alleviating or ameliorating at least one physical parameter including those which may not be discernible by the patient.

Unless otherwise defined herein, scientific, and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, and protein and nucleic acid chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Various embodiments of the disclosure are described herein. It will be recognized that features specified in each embodiment may be combined with other specified features, including as indicated in the embodiments below, to provide further embodiments of the present disclosure.

The microfluidic tumor-on-a-chip system described herein is to be used after a patient is diagnosed with a disease or disorder, particulary cancer (which may be pathogenic or benign). Cells from the tumor biopsy can be obtained from the pathology lab, grown in the system, and screened against multiple drugs in up to two weeks. The results would be conveyed to the primary oncologist allowing them to make a better-informed decision on which drug they decide start the chemotherapy with first. This personalized approach would improve the efficacy of chemotherapy and reduce the time and costs that are associated with treatments.

Patient-derived microtumors can be grown and preserved inside the optimized hydrogels described herein for up to two weeks in vitro. The microtumor represents the real tumor environment at a cellular and molecular level. The scaffolding structure of the microfluidic chips, the multi-hydrogels, and the continuous controlled supply of nutrition and oxygen allow for the cancer cells to grow and function similar to their in vivo performance. The platform described herein allows multiple combinations of potential chemotherapy drugs to be screened allowing the evaluation of optimal combinations for treatment. Various doses can also be tested to determine effective doses for particular patients. This information would allow oncologists to determine more effective treatment strategies.

Described herein is a tumor-on-a-chip device or system, which can grow a subject's tumor biopsy-derived cancer cells outside the body. Tumor spheroids can be formed in the hydrogel environment allowing the growth and viability of the cells to be monitored. With this system, microtumors can be produces inside the microfluidic chip, creating a platform that can test the efficacy of chemotherapeutic drugs against a subject's own cancer cells. The ultimate goal is to offer personalized cancer screening based on this technology and evaluate the different possible treatments prior to starting chemotherapy.

Growing ex vivo microtumors from a subject's cancer cells in the system described herein is done within a 2-week period and the device provides a substrate to test the possible treatments for the chemotherapy. The unique design allows the growth of patient-derived cancer cells as spherical microtumors with predefined sizes and shapes. The characteristics of the microtumors can be monitored and the efficacy of the drugs can be determined based on an individualized basis. This device could be utilized in hospitals, and cancer centers and institutes where it would improve the success rates of chemotherapy, reduce the costs and duration of treatment, and provide a personalized prescription for each patient. Pharmaceutical R&D departments and laboratories that work in the field of cancer would also benefit from the devices described herein by using them to evaluate their newly developed drugs and drug delivery systems. This will improve the accuracy of their results and reduce the costs and time of testing.

The device described herein can provide results with greater accuracy, at lower costs and faster turnaround times, than current devices. A significant advantage of the disclosed device is its ability to test multiple drugs, each at varying doses. This is not offered in any of the current clinical systems. This allows the selection of optimal forms of treatment for the patients, hence reducing failure rates.

Figure 1B:
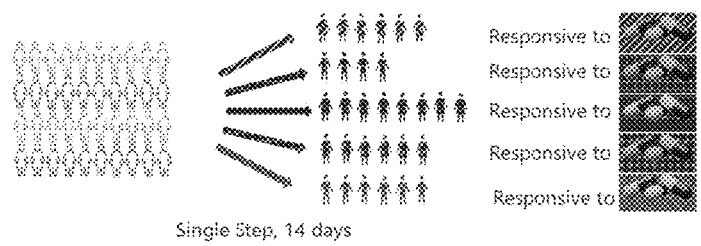
FIG. 1B shows the process using a multigel single step tumor-on-a-chip platform as described herein.
Figure 2:
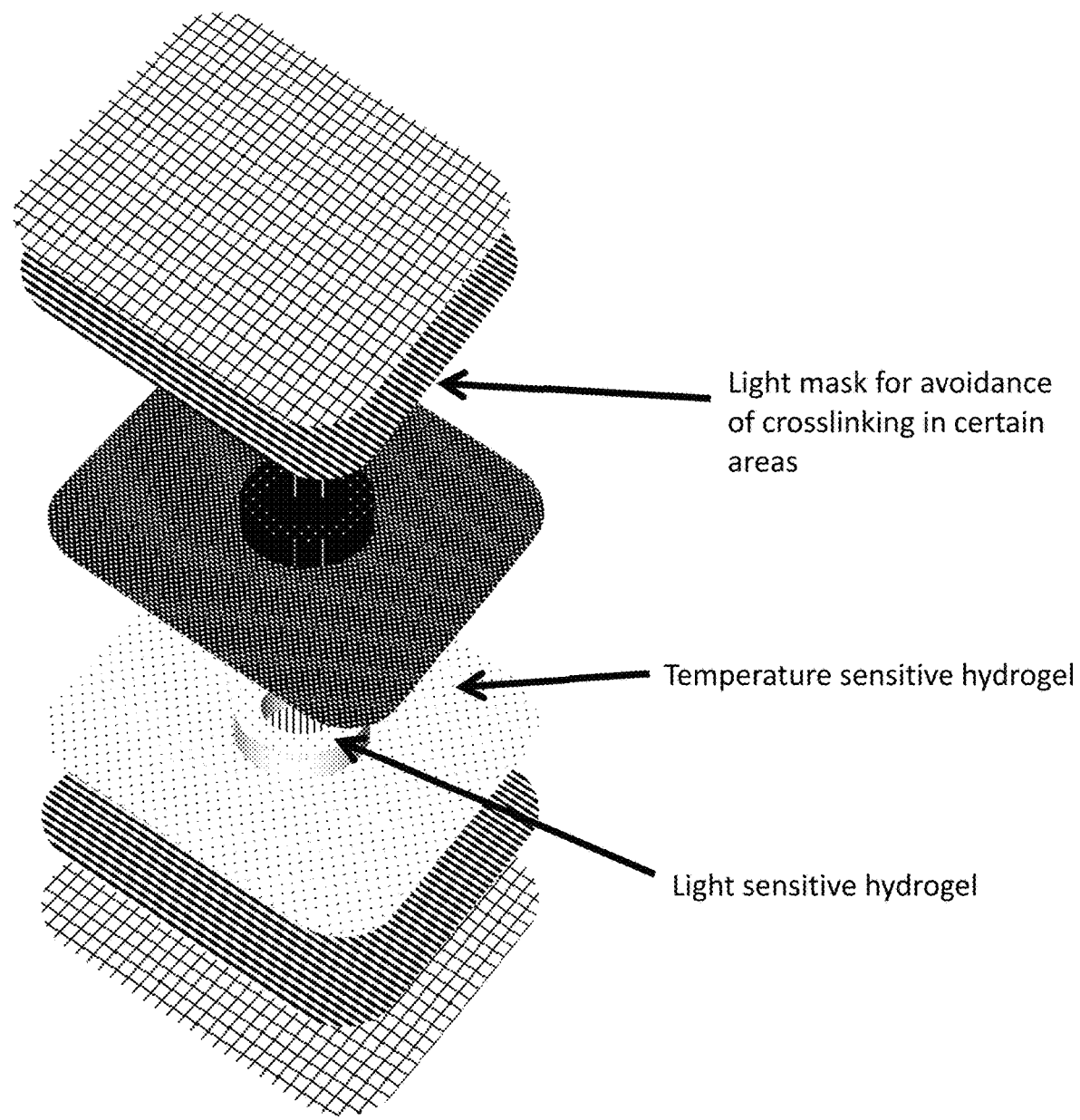
FIG. 2 shows an exemplary schematic of the layer-based technology with a multigel fabrication system.
Figure 3:
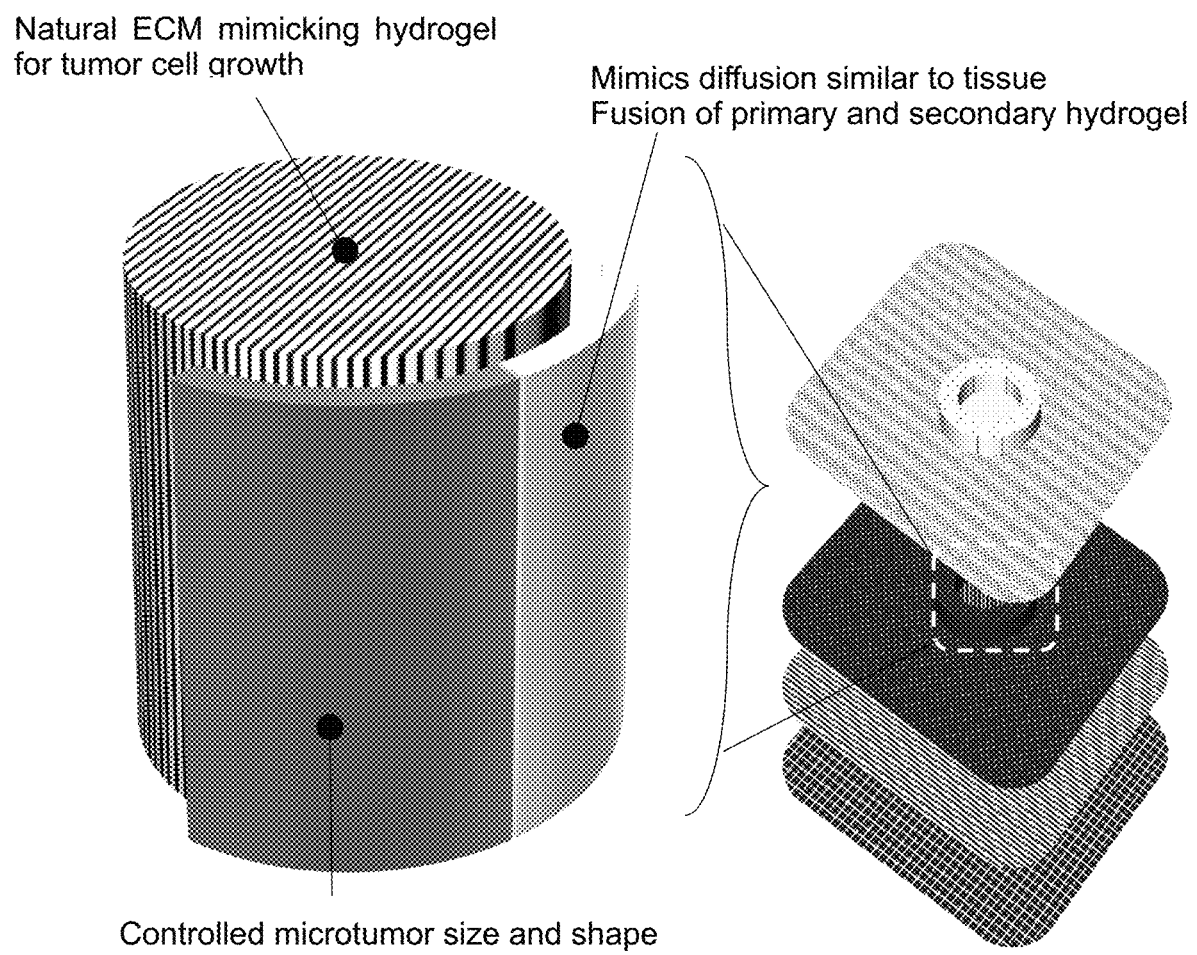
FIG. 3 shows an exemplary schematic of the characteristics of the multi-gel tumor-on-a-chip system allowing for spherical microtumor growth.
Figure 4A:
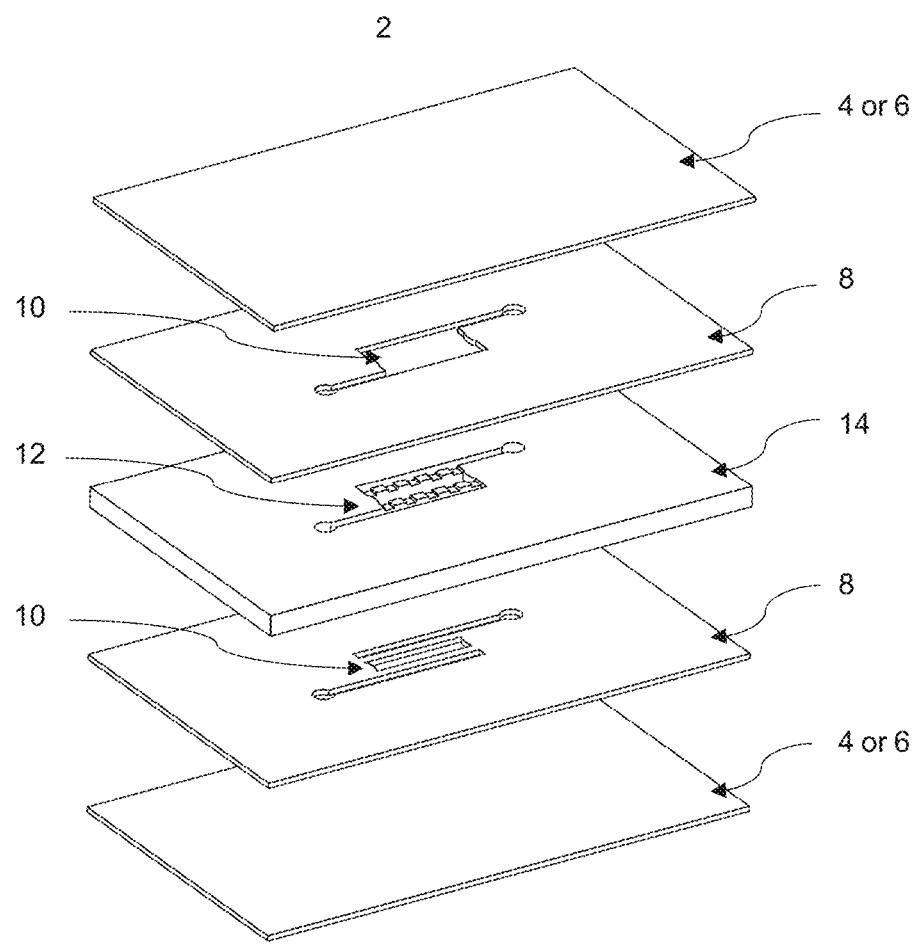
FIG. 4A shows an exemplary schematic showing the layer-by-layer outline of the linear design of the multigel tumor-on-a-chip microfluidic device.
Figure 4B:
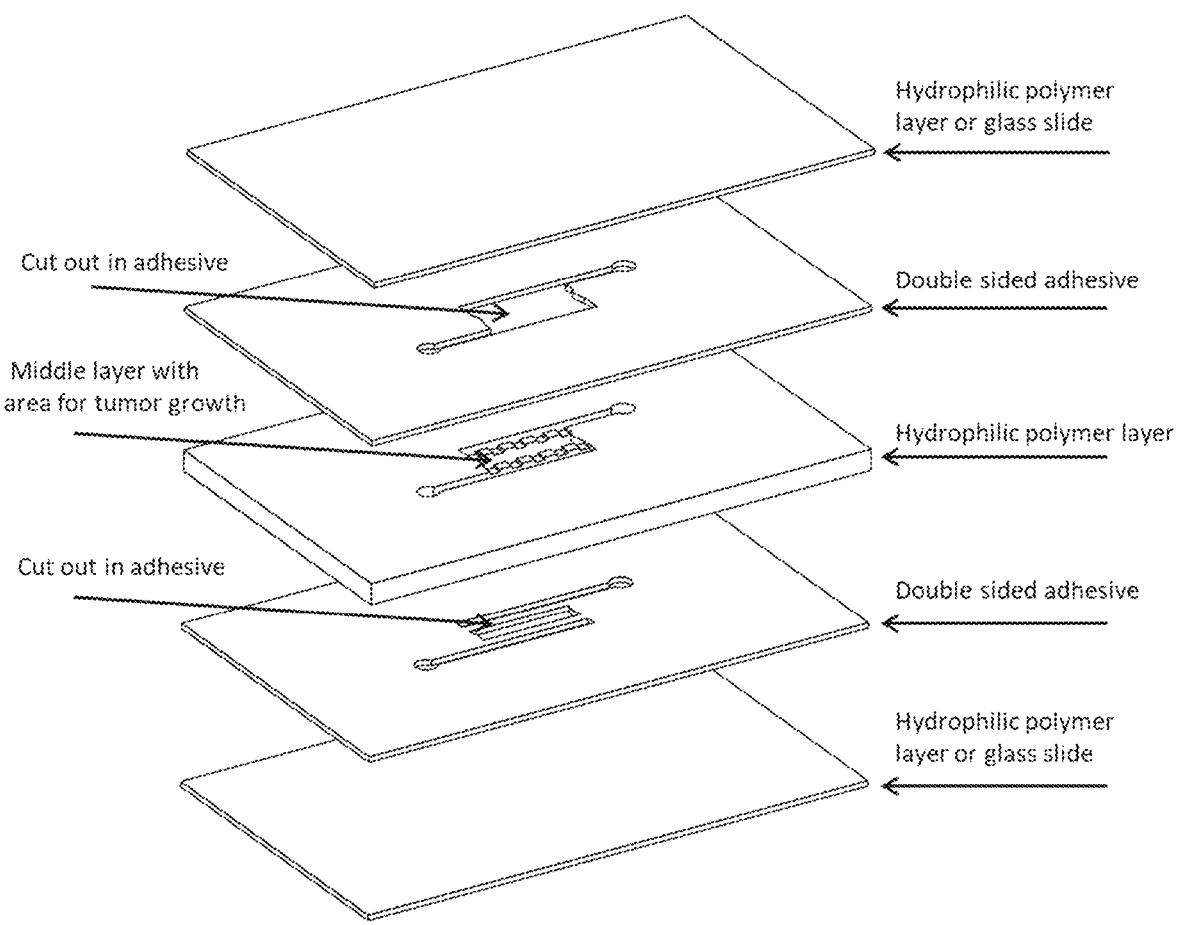
FIG. 4B shows the same schematic with labels.
Figure 5A:
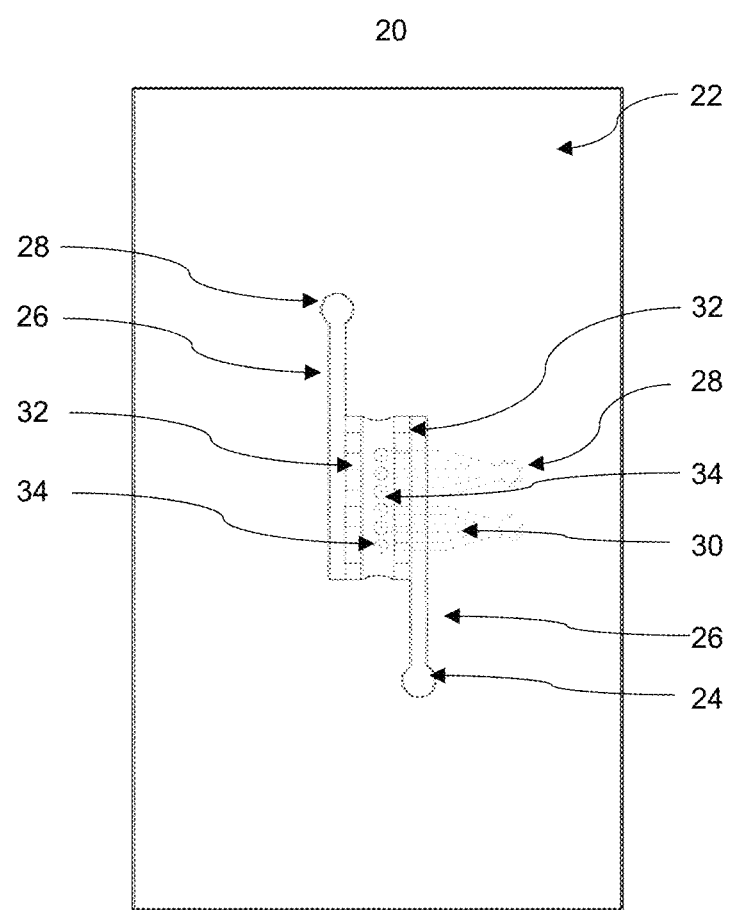
FIG. 5A shows an exemplary schematic of the top view of the N-shaped design of the multigel tumor-on-a-chip for the microfluidic device.
Figure 5B:
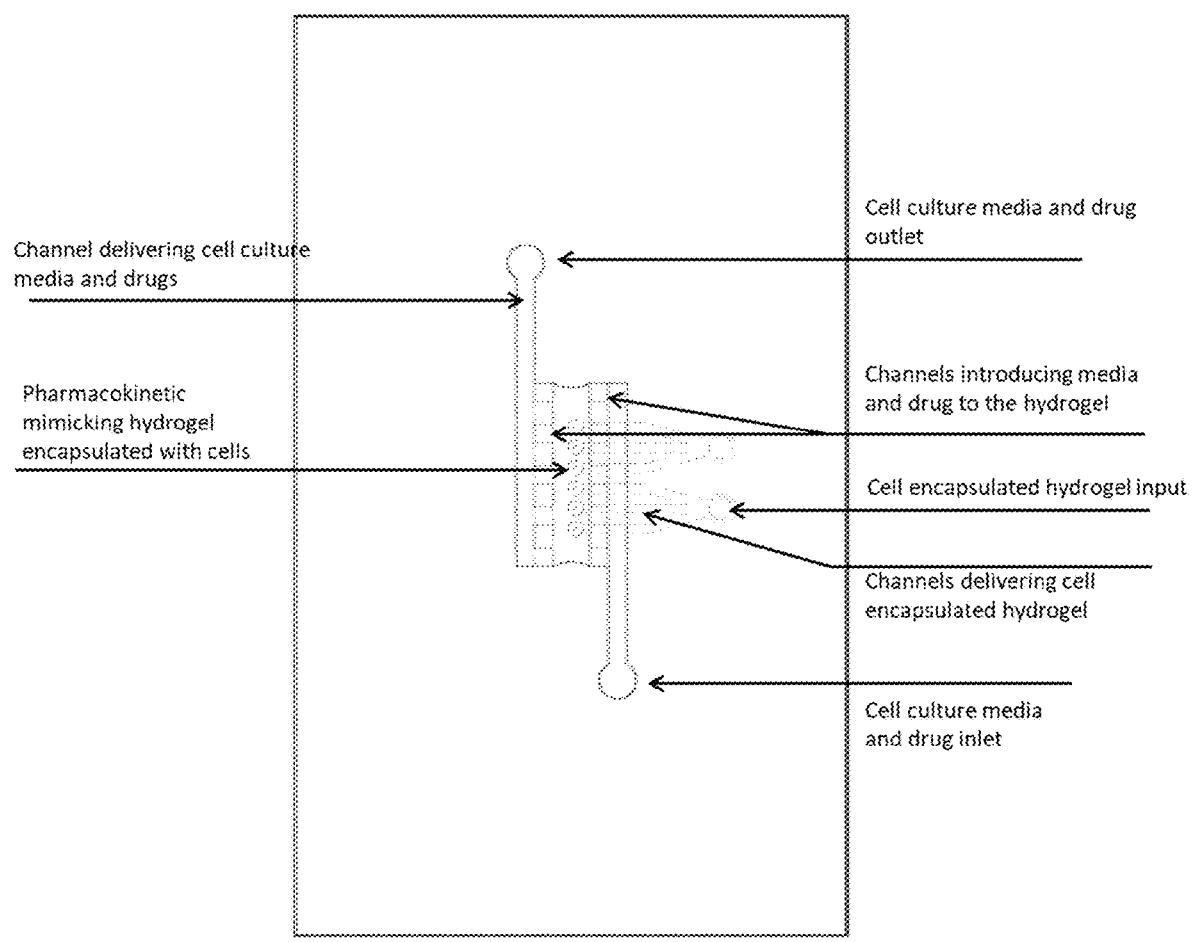
FIG. 5B shows the same schematic with labels.
Figure 6A:
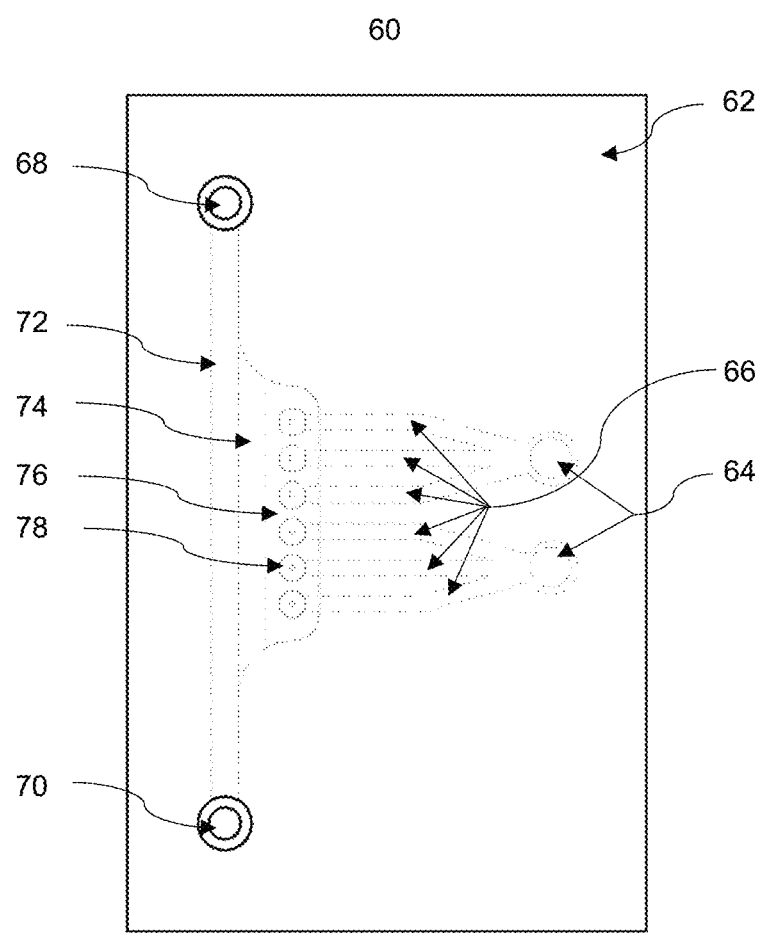
FIG. 6A shows an exemplary schematic of the middle layer of the microfluidic system. This layer is the main space for tumor growth. The remaining parts of the device can be fabricated via the layer-by-layer fabrication method.
Figure 6B:
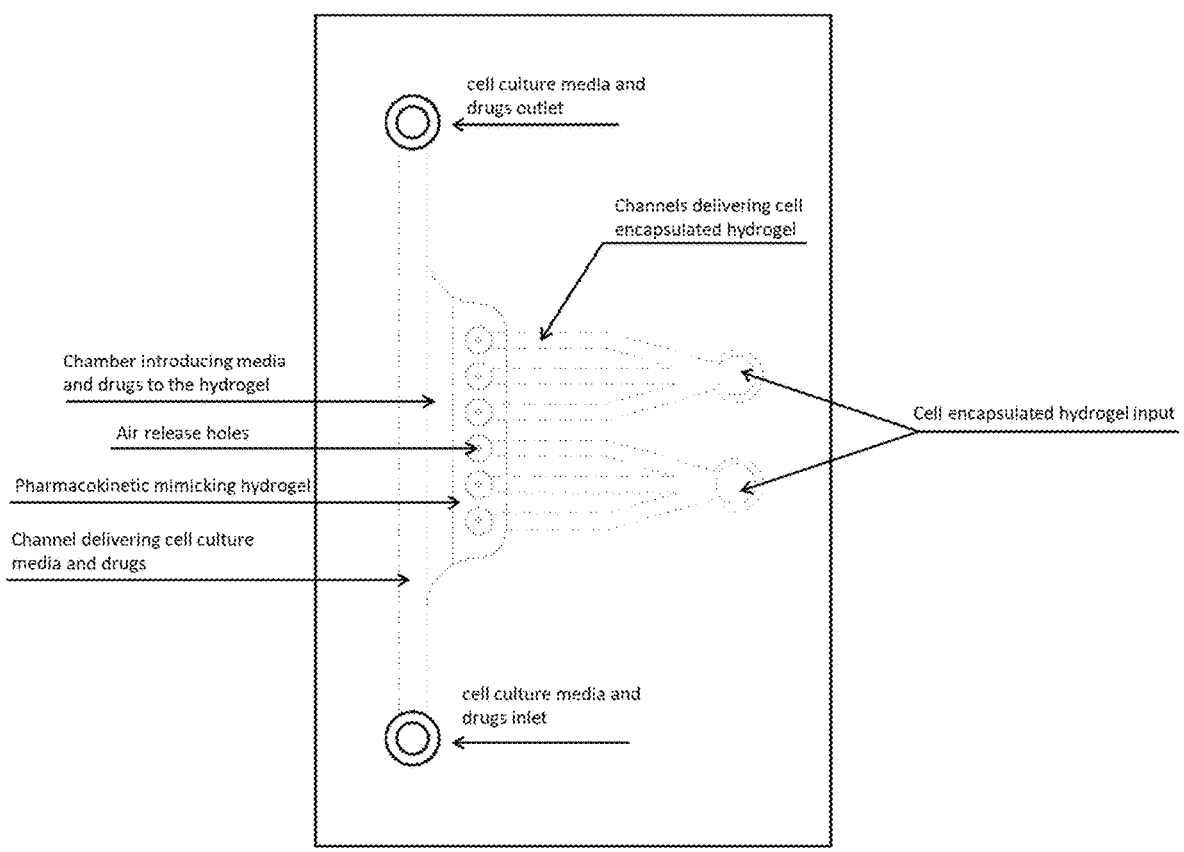
FIG. 6B shows the same schematic with labels.
Figure 7A:
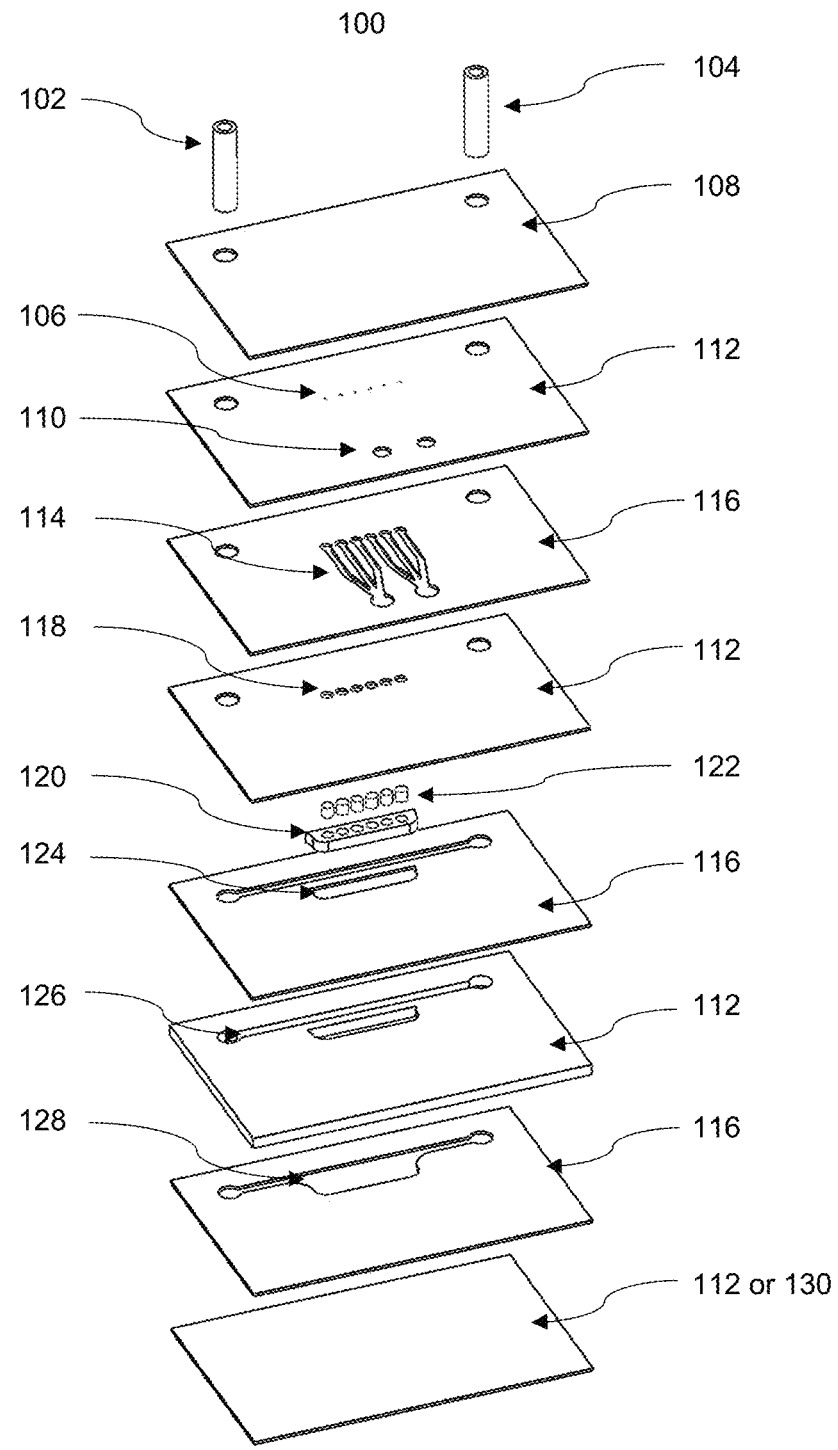
FIG. 7A shows an exemplary schematic showing an exemplary model of the microfluidic device.
Figure 7B:
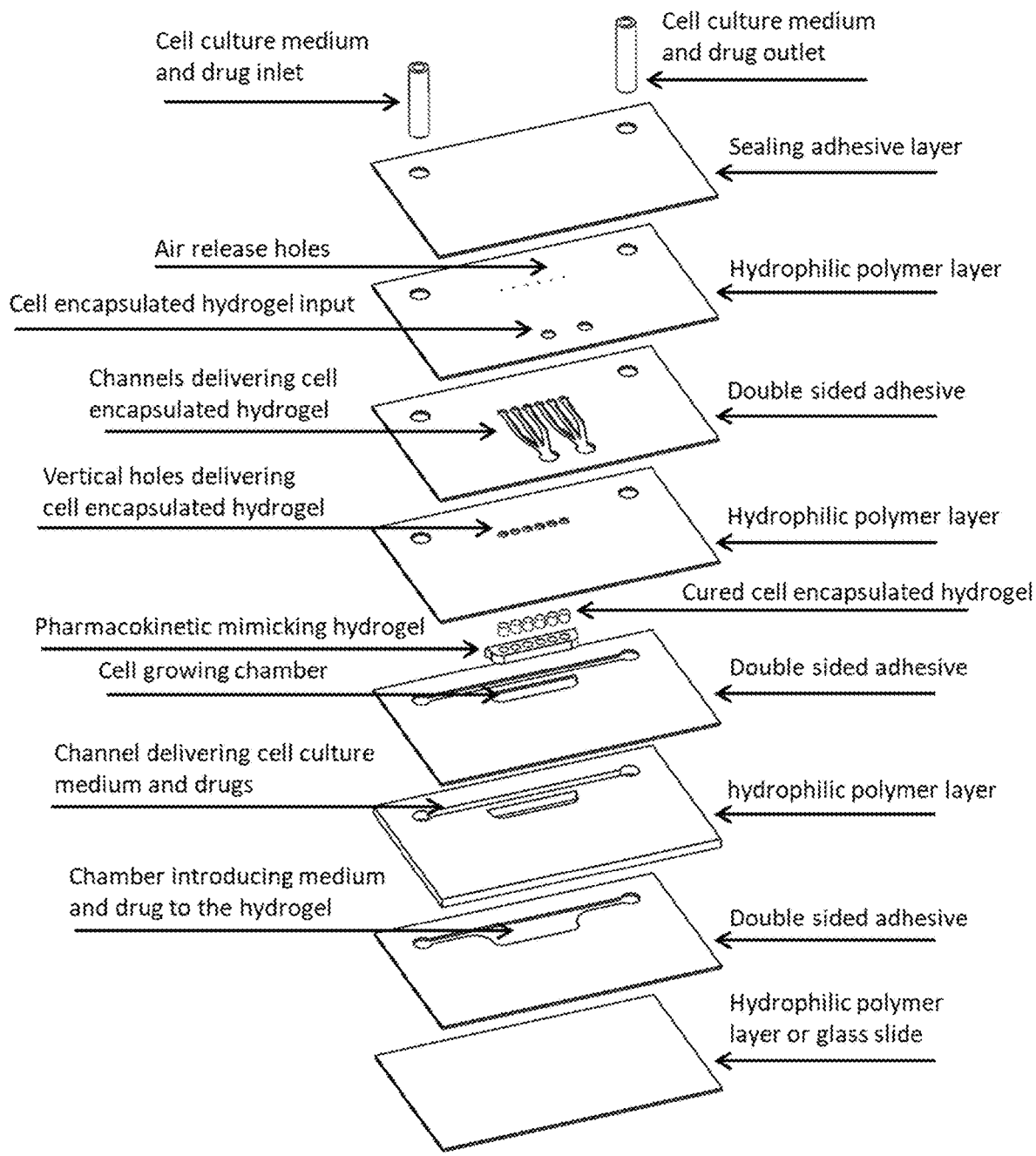
FIG. 7B shows the same schematic with labels.

FIG. 1 illustrates the current process of treatment (top) compared to the process proposed for using the device described herein (bottom).

Described herein is a three-dimensional (3D) multi-tumor-on-a-chip microfluidic device to screen drugs against certain types of cancer. The device or system includes:
a single step tissue-on-a-chip platform to be used in clinics, labs, and pharmaceutical research and development. The described process requires mixing the cells with thermoset hydrogels (e.g., solubilized basement membrane preparation (Matrigel®), gelatin methacrylamide (GelMA), gelatin, agar, agarose, carrageenan, inter alia) or light-curable hydrogels (e.g., 4-arm-PEG acrylate) and introducing the combination to the chip. This delivers the cells to the chambers allowing continuous growth;

A multi-gel extracellular structure for mimicking the pharmacokinetics of drug delivery;

a mechanism that controls the initial size of the cylindrical or spherical tumor, with a clear boundary, enabling accurate monitoring and measuring of tumor size and growth;

a multilayer device fabrication allowing simple modifications to scale-up for various applications; and a unique design with a combination technique for multiple hydrogels that produce measurable predefined microtumor structures suitable for screening drugs.

See FIG. 2-7.

A key factor in cancer treatment and drug therapy is the development of biomimetic devices that are capable of replicating the living body. These devices supply researchers and clinicians with prediction models and tools to make better and more informed decisions. The majority of the cell studies so far have been based on 2D cell culture systems or static 3D models. The inability of these systems to mimic the in vivo conditions, in addition to the challenges associated with their clinical translation and adoption limit their usage.

Described herein is a multi-layered microfluidic device, compatible with mass-scale fabrication criteria, which can grow cancer cells in 3D and mimics the diffusion in human tumor environments. Studies have been conducted with human ovarian cancer cell lines (OVCAR8) and human lung cancer cell lines (A549) that were embedded in two different hydrogels. A UV photo-crosslinkable 4-arm poly(ethylene glycol) acrylate (4-arm PEG acrylate) (molecular weight: 2000 kDa) was used as a hydrogel (hydrogels with alternative curing mechanisms can be used) to form the matrix surrounding the encapsulated cells. The second type of hydrogel for encapsulating and growing cells was the thermosensitive hydrogel, a solubilized basement membrane preparation (Matrigel®), or other thermo curable hydrogels such as a gelatinous protein mixture, gelatin methacrylamide (GelMA), gelatin, fibrin, agarose, agar, chitosan, carrageenan, inter alia. In addition, nano-scale drug delivery systems were combined with the platform to evaluate the transportation of the nanoparticles. Two distinct fluorescently labeled self-assembled lipid nanoparticles (nanodiscs and nanovesicles with and without conjugated active targeting tags) were investigated in the microchannels under constant flow conditions. The goal of this particular experiment was to prove that this system permits diffusion of large drug carriers, like nanocarriers, to the core tumor. Regular chemotherapy involves small molecules with a $1/100$ of the size of these two nanocarriers. Therefore, because nanodiscs (AKA: Bicelle) and nanovesicles (AKA: Liposome) diffuse into the microtumors, this system can be used to evaluate small molecule chemotherapies, nanomedicine therapies, and biomolecule therapies.

These microfluidic devices can be fabricated using rapid prototyping. For example, the microfluidic devices can be fabricated using one or more of laser cutting the hydrophilic substrates, die cutting, milling, press cutting, layer-by-layer fabrication, 3D printing, or lithography. The design protocol can also be easily configured to adapt and create highly controlled microenvironments for different cell lines. The devices allow direct imaging of the cells using an optical microscope, fluorescent microscope, or other imaging methods. Further the spent culture media or cells can be removed and analyzed using a variety of biochemical methods such as flow cytometry, apoptotic assays, ELISA, radioimmunoassays, or PCR-based assays, inter alia.

One embodiment described herein is a multi-layer, multi-gel microfluidic device 2, comprising: a plurality of layers (4 or 6, 8, 14, 8, 4 or 6). See FIG. 4A-B. In one aspect, the top and bottom layers 4 or 6 comprise a hydrophilic polymer layer 4 or a glass layer 6. The middle layer 14 is a hydrophilic polymer layer. Sandwiched between the top and bottom hydrophilic polymer layer 4 or glass layer 6 and the middle hydrophilic polymer layer 14, are adhesive layers 8, which contain cutouts 10 that provide fluid communication with the middle layer 14. The middle layer 14 contains an area 12 having plurality of spaces for hydrogel and tumor growth.

Another embodiment described herein is a middle layer 20 of the multi-layer, multi-gel microfluidic device described herein. See FIG. 5A-B. In one aspect, the middle layer 20 comprises a hydrophilic polymer layer 22. The hydrophilic polymer layer 22 is fabricated by laser cutting, die cutting, milling, press cutting, layer-by-layer fabrication, 3D printing, or lithography to provide an internal space, channels, inlets, and outlets for housing hydrogels and cells for growth and providing media and drugs. In one aspect, the middle layer comprises one or more inlets 24, outlets 26, fluidly connected by one or more channels 26 for delivering or releasing cell culture media or drugs. The central portion of the middle layer contains a plurality of spaces for housing hydrogels and cells for growth 34 which are in fluid communication with channels 32 in fluid connection with the one or more channels 26 for delivering or releasing cell culture media or drugs. A separate set of inlets 28 are in fluid communication via channels 30 with the plurality of spaces for housing hydrogels and cells for growth 34 and permit the introduction of the hydrogel and hydrogel cell mixture into the spaces 34.

Another embodiment described herein is a middle layer 60 of the multi-layer, multi-gel microfluidic device described herein. See FIG. 6A-B. In one aspect, the middle layer 60 comprises a hydrophilic polymer layer 62. The hydrophilic polymer layer 62 is fabricated by laser cutting, die cutting, milling, press cutting, layer-by-layer fabrication, 3D printing, or lithography to provide an internal space, channels, inlets, and outlets for housing hydrogels and cells for growth and providing media and drugs. In one aspect, the middle layer comprises one or more inlets 70, outlets 68, fluidly connected by one or more channels 72 for delivering or releasing cell culture media or drugs. The central portion of the middle layer contains a plurality of spaces for housing hydrogels and cells for growth 76 which are in fluid communication with a chamber 74 in fluid connection with the one or more channels 72 for delivering or releasing cell culture media or drugs. A separate set of inlets 64 are in fluid communication via channels 66 with the plurality of spaces for housing hydrogels and cells for growth 76 and permit the introduction of the hydrogel and hydrogel cell mixture into the spaces 76. The spaces for housing hydrogels and cells for growth 76 have one or more gas release ports 77 for releasing gases produced by the cells.

Another embodiment described herein is a multi-layer, multi-gel microfluidic device 100, comprising: a plurality of layers (108, 112, 116, 130) comprising a plurality of inlets 102, 110, outlets 104, and channels (114, 126) in fluid communication, and a middle layer comprising a cell growing chamber 124 in fluid communication with a culture medium channel 126, the cell growing chamber 124 comprising a first cured hydrogel 120, wherein the first uncured hydrogel provides a plurality of uncured spaces, the uncured space capable of being filled with a population of tumor cells encapsulated in a second cured hydrogel 122; a cell culture medium inlet 102 and outlet 104 in fluid communication with each other via a cell culture medium channel 126, and one or more cell encapsulated hydrogel inputs 110, in fluid communication 118 with a plurality of cell encapsulated microgel delivery channels 14 and the cell growing chamber 24. See FIG. 7A-4B.

In one aspect, the surface of the device has a cell culture media and drug inlet 102 and a sell culture media and drug outlet 104. This layer is sealed by an adhesive layer 108 to a hydrophilic polymer layer 112 that comprises one or more air release ports 106. A next layer has input ports for hydrogel encapsulated cells 110 and is attached to the layer above and below via a double-sided adhesive layer 116 comprising channels for delivering hydrogel encapsulated cells 114. A next hydrophilic polymer layer 112 comprises vertical ports for delivering population of tumor cells encapsulated in a cured hydrogel 122. The middle layer comprises one or more chambers enclosing second hydrogel encapsulated cells 22 and a first pharmacokinetic mimicking hydrogel 120. Below this layer is a double-sided adhesive layer 116 comprising a cell growing chamber 124. A further hydrophilic polymer layer 112 comprises one or more channels for delivering cell culture media and drugs 126 to the population of tumor cells encapsulated in a cured hydrogel 122. Below this layer is another double-sided adhesive layer 16 comprising a chamber for introducing media and drug to the hydrogel 128. The bottom layer comprises either a hydrophilic polymer layer 112 or glass slide 130.

In one aspect, the plurality of hydrophilic layers comprises hydrophilic polymer sheets comprising one or more of polyacrylic acid, polymethylmethacrylate, polycarbonate, polyester, nylon, polyvinyl chloride, polyethylene, polypropylene, polyethylene terephthalate glycol, polybutylene adipate terephthalate, ethylene tetrafluoroethylene, fluorinated ethylene propylene, perfluoro alkoxy alkane, polylactic acid, polycaprolactone, polyoxymethylene, cellulose, co-polymers thereof, or combinations thereof. In another aspect, the bottom layer is glass.

In another embodiment, the first cured hydrogel comprises uncured spaces comprising one or more of cylindrical, spherical, cubic, or other shaped voids that can be occupied by a population of tumor cells encapsulated in the second cured hydrogel.

In one aspect, either of the hydrogels can comprise a light- or thermally cured hydrogel including a 4-arm polyethylene glycol acrylate, a gelatinous protein mixture, gelatin methacrylamide (GelMA), gelatin, fibrin, agarose, agar, chitosan, carrageenan, solubilized basement membrane preparation (Matrigel®), among others.

In another aspect the first cured hydrogel comprises a 4-arm polyethylene glycol acrylate, gelatin, fibrin, or a combination thereof that are curable using UV/visible light.

In another aspect, the second cured hydrogel comprises one or more of a solubilized basement membrane preparation (Matrigel®, Corning), a gelatinous protein mixture, gelatin methacrylamide (GelMA), gelatin, fibrin, agarose, agar, chitosan, carrageenan, or combination thereof. In one aspect, the second hydrogel is a solubilized basement membrane preparation extracted from the Engelbreth-Holm-Swarm (EHS) mouse sarcoma, a tumor rich in such ECM proteins as laminin (a major component), collagen IV, heparan sulfate proteoglycans, entactin/nidogen, and a number of growth factors (e.g., Matrigel Matrix, Corning). Generally, these hydrogels are heated and then cure upon cooling. Tumor cells can be mixed with the warmed second hydrogel and injected into the interstitial space of the first hydrogel in the microfluidic device as described herein. Upon cooling the second hydrogel encapsulates the tumor cells forming a tissue-like structure in conjuction with the first hydrogel.

In another aspect, first and second cured hydrogels are cured by different mechanisms. In one aspect, the first cured hydrogel is UV-cured. In another aspect, the second cured hydrogel is thermally cured. In one aspect, the curing of the hydrogel does not damage the tumor cells.

The advantage of the system described herein is that the tumor cells are encapsulated in a hydrogel matrix that replicates the tissue environment of a subject's body. This provides a confined space and permits diffusion of chemotherapeutic drugs in a manner similar to the natural three-dimensional environment of the organism. The system described herein can also be used as a research tool for investigating new chemotherapeutics on a variety of cell or tumor types.

Tumor cells from a subject can be obtained through needle punch biopsies, surgical excision, or other means known in the art. In other aspects, human or animal cell lines or tumors can be used. Only small number of cells are required (ca. 100) to seed the multiple wells of the system. The system described herein provides the ability to grow multiple tumors or cells from a single sample and test chemotherapeutic drugs or combinations thereof to determine which drugs and the dosages thereof are most efficacious in inhibiting tumor growth or viability (i.e., killing the tumor). Multiple replicates can be conducted with a single device. The dosage, dosing regimen, combinations, and other factors can be investigated ex vivo prior to administering the chemotherapeutic to the subject. This permits high-throughput personalized medicine testing of chemotherapeutics to identify which chemotherapeutics and the dosages that are most efficacious for a particular subject's tumors.

One embodiment described herein is a rapid and reproducible method for the dissociation, growth, and cryopreservation of viable tumor tissue from patients undergoing tumor removal surgery or tumor biopsy. See FIGS. 4-7; 19-20. Specimens from subjects were obtained through surgery or needle biopsy procedure, with the subject's informed consent. Samples for these studies must be fresh or frozen un-fixed samples; approximately 50-500 mg of the biopsy (or tumor) is required. Specimens were trimmed to remove surrounding tissue and cut into multiple 0.5-mm-thick slices, using a Stadie-Riggs microtome (A.H. Thomas Co., Philadelphia, Pa.). The tissues were minced with a scalpel into approximately ~1 mm$^3$ pieces and washed with Hank's balanced salt solution. The tissue samples were digested with an enzymatic cocktail (e.g., one or more of 300 U/mL collagenase, 100 U/mL hyaluronidase, or DNase 100,000 U/mL) at 37° C. with gentle stirring. After digestion, the tissue suspensions were separated and used in preparation of the hydrogels for the devices as described herein. Treatment trials were performed after consultation with oncologists, using selected types and dosages of cancer chemotherapeutics, and cellular responses such as cytotoxicity, resistivity, phosphorylation, protein expression, apoptotic cell cycle, inter alia, were evaluated.

Drugs that can be tested in the system include chemotherapeutic drugs or agents, cytotoxins, antibiotics, anti-viral agents, immunomodulatory agents, or anti-inflammatory agents. In one embodiment, the chemotherapeutic drug or agent comprises one or more of alkylating agents, antimetabolites, anti-tumor antibiotics, topoisomerase inhibitors, mitotic inhibitors, platinum-based agents, or biologics (e.g., antibody-based therapeutics). In one aspect, the chemotherapeutic drug or agent comprises one or more of Abiraterone acetate, Albumin-bound (nab) paclitaxel, Alemtuzumab, Altretamine, Belinostat, Bendamustine, Bevacizumab, Bleomycin, Blinatumomab, Bortezomib, Brentuximab vedotin, Busulfan, Cabazitaxel, Capecitabine, Carboplatin, Carmustine, Ceritinib, Cetuximab, Chlorambucil, Cisplatin, Cladribine, Crizotinib, Cyclophosphamide, Cytarabine (Ara-C), Dabrafenib, Dacarbazine, Dactinomycin, Dasatinib, Daunorubicin, DaunoXome (liposomal daunorubicin), DepoCyt (liposomal cytarabine), Docetaxel, Doxil (liposomal doxorubicin), Doxorubicin, Epirubicin, Eribulin mesylate, Erlotinib, Estramustine, Etoposide, Everolimus, Floxuridine, Fludarabine, Fluorouracil, Gefitinib, Gemcitabine, Gliadel, Hydroxyurea, Ibritumomab, Ibrutinib, Idarubicin, Idelalisib, Ifosfamide, Imatinib, Ipilimumab, Irinotecan, Ixabepilone, Lanreotide, Lapatinib, Lenalidomide, Lenvatinib, Lomustine, Mechlorethamine, Melphalan, Mercaptopurine, Methotrexate, Mitomycin, Mitoxantrone, Nilotinib, Nivolumab, Ofatumumab, Olaparib, Oxaliplatin, Paclitaxel, Palbociclib, Panitumumab, Panobinostat, Pazopanib, PEG-asparaginase, Pembrolizumab, Pemetrexed, Pentostatin, Pralatrexate, Procarbazine, Ramucirumab, Rituximab, Romidepsin, Ruxolitinib, Sipuleucel-T, Sorafenib, Streptozocin, Sunitinib, Temozolomide, Temsirolimus, Teniposide, Thalidomide, Thioguanine, Thiotepa, Topotecan, Tositumomab, Trametinib, Trastuzumab, Valrubicin, Vandetanib, Vemurafenib, Vinblastine, Vincristine, Vinorelbine, or combinations thereof.

Specific cancer or tumor cell types include those of carcinoma, lymphomas, sarcomas, or leukemias. In one embodiment, the cancer or tumor cell comprises a malignancy of the connective tissue, endothelium, mesothelium, blood or lymphoid cells, muscle, or epithelial tissues. neural tissue, amine precursor uptake and decarboxylation system, other neural crest-derived cells, or gonadal tissue. In one aspect, the tumor cells or tumor comprises one or more of fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, leukemia, of various types; aleukemic leukemia, multiple myeloma, Hodgkin lymphoma, non-Hodgkin lymphoma, leiomyosarcoma, rhabdomyosarcoma, squamous cell carcinoma, epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma, anaplastic, glioblastoma multiforme, ganglioneuroma, neuroblastoma, medulloblastoma, malignant meningioma, malignant Schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, malignant paraganglioma, melanoma, Merkel cell neoplasm, cystosarcoma phylloides, Wilms tumor, seminoma, dysgerminoma, choriocarcinoma, embryonal carcinoma, endodermal sinus tumor, or teratocarcinoma. Other cell lines from humans (e.g., HeLa cells) or animals can also be used for testing chemotherapeutics or other drugs.

Another embodiment described herein is a method for monitoring cell growth and viability, the method comprising: isolating cells from a subject or a human or animal cell line; encapsulating the cells in a curable hydrogel; inserting the encapsulated cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of cells encapsulated in a second cured hydrogel; incubating the encapsulated cells in the microfluidic device under conditions favorable for cell growth for a period of time; and analyzing the encapsulated cells in the microfluidic device. In one aspect, the method further comprises contacting the encapsulated cells with fluorescently labeled species comprising one or more of small molecules, nanoparticles, nanoparticles comprising nanodiscs, nanovesicles, or liposomes; and analyzing the nanoparticles. In another aspect, the analyzing comprises light microscopy, fluorescence microscopy, other imaging methods, flow cytometry, immunohistochemistry, immunofluorescence, histological analysis, in situ hybridization techniques, apoptotic assays, ELISA, radioimmunoassays, proteomic approaches (targeted or shotgun-based), or PCR-based assays. In another aspect, the method further comprises determining viability of the encapsulated cells.

Another embodiment described herein is a method for determining the effect of drugs on cell viability, the method comprising: isolating cells from a subject or a human or animal cell line; encapsulating the cells in a curable hydrogel; inserting the encapsulated cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of cells encapsulated in a second cured hydrogel; incubating the encapsulated cells in the microfluidic device under conditions favorable for cell growth for a period of time; and analyzing the encapsulated cells in the microfluidic device. In one aspect, the method further comprises contacting the encapsulated cells with one or more drugs for a period of time; incubating the encapsulated cells for a period of time; and analyzing changes or the reduction in viability of the contacted encapsulated cells after the incubation period.

In one aspect the period of time comprises enough time to evaluate the viability of the cells and permit the cells to grow into a microtumor. In another aspect, the period of time comprises the time required after administration of one or more drugs to determine the effect of the drug on the tumor viability or lack thereof. In one aspect, the period of time is from about 1 day to about 60 days, including all integers within the range and the end points. In another aspect the period of time is about 2 days, 4 days, 6 days, 8 days, 10 days, 12 days, 14 days, 16 days, 18 days, 20 days, 22 days, 24 days, 26 days, 28 days, or 30 days. In another aspect the period of time is about 1 week, 2 weeks, 3 weeks, 4 weeks, 5 weeks, 6 weeks, 7 weeks, 8 weeks, 9 weeks, or 10 weeks, including all integers (days) within the week periods. In another aspect, the cells are incubated in the device for about 1 to 3 weeks (e.g., about 7 to about 21 days) including all integers (days) within the week periods, to replicate the tumor; and then after administration of one or more drugs, the cells are evaluated for an additional period of about 1 to 3 weeks (e.g., about 7 to about 21 days) including all integers (days) within the week periods.

In one aspect described herein, the drugs comprise chemotherapeutic drugs or agents, cytotoxins, antibiotics, antiviral agents, immunomodulatory agents, or anti-inflammatory agents. In another aspect, the drugs comprise anti-cancer chemotherapeutics. In another aspect, the contacting the encapsulated cells with one or more drugs comprises a sequential or stepwise administration of the one or more drugs. In another aspect, the method further comprises initiating, maintaining, or modifying therapeutic treatment or dosage thereof of a subject from whom the cells were obtained based on the analysis of the encapsulated cells.

Another embodiment described herein is a method for evaluating the efficacy of a chemotherapeutic treatment on a subject's tumor, the method comprising: isolating tumor cells from a subject's tumor; encapsulating the tumor cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; evaluating the efficacy of the chemotherapeutic drug on the encapsulated tumor cells; and initiating, maintaining, or modifying chemotherapeutic treatment and dosage thereof of the subject from whom the tumor cells were isolated. In one aspect, the contacting comprises a single, sequential, or stepwise administration of one or more chemotherapeutic drugs. In another aspect, the chemotherapeutic drug comprises one or more of alkylating agents, antimetabolites, anti-tumor antibiotics, topoisomerase inhibitors, mitotic inhibitors, platinum-based agents, or biologics.

Another embodiment described herein is a method for screening the effectiveness of a chemotherapeutic drug on a tumor cell, the method comprising: obtaining tumor cells from one or more subjects or established tumor cell lines; encapsulating the tumor cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; incubating the encapsulated tumor cells in the microfluidic device under conditions favorable for tumor cell growth for a period of time; contacting the encapsulated tumor cells with one or more chemotherapeutic drugs for a period of time; analyzing changes or viability in the encapsulated tumor cells after the period of time; and evaluating the effectiveness of the chemotherapeutic drug on diminishing the viability of the encapsulated tumor cells. In one aspect, the contacting comprises a single, sequential, or stepwise administration of one or more chemotherapeutic drugs.

Another embodiment described herein is a method of manufacturing a multi-layer, multi-gel microfluidic device, comprising: fabricating a plurality of layers, the layers defining a cell growing chamber in fluid communication with a culture medium channel, a cell culture medium inlet and outlet in fluid communication with each other via the cell culture medium channel, and one or more cell encapsulated hydrogel inputs in fluid communication with a plurality of cell encapsulated microgel delivery channels and the cell growing chamber, depositing a first hydrogel in the cell growing chamber and curing in manner to provide a cured first hydrogel with a plurality of uncured spaces comprising one or more cylindrical wells, depositing a population of cells in a second hydrogel into the uncured spaces and curing the second hydrogel to provide a population of cells encapsulated in a second cured hydrogel, assembling the multilayer device, and assembling connectors and tubes. In one aspect, the fabrication is by one or more of laser cutting, die cutting, milling, press cutting, layer-by-layer fabrication, 3D printing, lithography, or combinations thereof.

Another embodiment described herein is a multi-layer, multi-gel microfluidic device manufactured by any of the methods described herein.

Another embodiment described herein is a multi-layer, multi-gel microfluidic device as shown in any of the Figures herein or described herein.

Another embodiment described herein is a method for isolation and preparation of cells from a subject for inclusion in a multi-layer, multi-gel microfluidic device as described herein. In one embodiment, process comprises a method for isolation and preparation of cells from a subject for inclusion in a multi-layer, multi-gel microfluidic device, the method comprising: obtaining tissue or a tumor from a subject's biopsy sample or surgical excision; placing the tissue or tumor in a medium for transport or temporary storage; removing the media; macerating the tissue in fresh media; pelleting the cells, removing the supernatant, and resuspending the cell pellet; incubating the resuspended cell pellet with enzymes for a period of time; pelleting the cells and removing the supernatant; optionally, resuspending the cell pellet, straining the cells with a cell strainer, and re-pelleting the cells; resuspending the cell pellet with warm media; counting the cells and diluting to a specific concentration; encapsulating the diluted cells in a curable hydrogel and inserting the cells in a multi-layer, multi-gel microfluidic device, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; and incubating the encapsulated tumor cells in the microfluidic device under conditions favorable for tumor cell growth for a period of time.

Another embodiment described herein is a multi-layer, multi-gel microfluidic device a kit comprising: one or more multi-layer, multi-gel microfluidic devices, comprising: a plurality of layers comprising a plurality of inlets, outlets, and channels in fluid communication, and a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel; a UV-curable hydrogel; a thermosettable hydrogel; tubing, syringes, and containers for preparation of the hydrogels, and introducing media or drugs into the device; optionally, culture media or chemotherapeutics drugs; sealed packaging; and instructions or directions for use.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

EXAMPLES

Example 1

Fabrication of Microfluidic Devices
The design and fabrication of the device includes these steps:
Rapid Prototyping including the three-dimensional design of five layers for the device. Each layer has at least three microfluidic channels (outer channel width=1100 μm, middle tumor-chamber=2200 μm). The devices were designed using Computer-aided design (CAD) program. The design transparencies were then printed by a commercial printer with the clear design and background ink. Transparencies were also used for the additional top and bottom layers and the connecting tapes. Each layer was designed in a way that the liquid gel is retained before curing and becoming solid.

The designs were micro-machined in 1.6 mm (1/16-inch) transparent clear polyacrylic substrates (middle), white polystyrene double-sided tapes, and poly methylmethacrylate covers, using a computer-controlled laser cutter (Epilog Legend $CO_2$ 65 W cutter, Epilog, Golden, Colo.).

For the light-sensitive hydrogel, 20 mg of 4-arm PEG acrylate 20K (PEG 20K) was mixed in 100 μL of phenol-free DMEM media and 1% photoinitiator (PI) (Irgacure 2959) was prepared by mixing 10 mg PI with 100 μL ethanol and 900 μL PBS.

The tumor-loaded chambers (circles in Schematic 5), can be produced with any hydrogels that are cured with heat, light, or other physical stimuli parameter curability, can be used unless the triggering factor does not damage the cells. Heat sensitive hydrogels such as a solubilized basement membrane preparation (Matrigel®) were used for these studies.

Matrigel® and tumor cells in growth media were mixed in a 4:1 ratio. The concentration of the cells in the media can vary depending the study timeline.

The microfluidic middle chamber was filled with the mixture, then cross-linked via UV irradiation for 30 sec at 7.0 mW/cm$^2$, leaving the desired pattern uncured (e.g., circular designs in Schematic 5, would be left uncured and will remain liquid, allowing these particular spaces to be filled with cell-loaded secondary hydrogels). After curing the polymer, uncured hydrogels were washed to remove the uncrossed gel and PI.

A 40 μL volume of Matrigel® was hydrated and kept in 4° C., mixed with cancer cells (at a concentration of at least 5,000 cells/mL). A droplet of 2 μL of the mixture was placed in the device after assembling the first three layers. The last two layers were then assembled and cured by heating at 37° C. for 20 min.

The rest of the device assembly was completed. All the connectors and tubes were connected.

The cells within the microfluidic device were incubated under 5% $CO_2$ at 37° C. Media was supplemented using a syringe pump at a constant flow rate. The formation of the microtumors and aggregation of cells within the hydrogel was evaluated and measured using a Zeiss Axiovert 40 CFL inverted microscope.

Tubing of 0.8 mm (1/32 inch) inner diameter was used to connect the syringe pump to load cells and inject media.

The pores were punched and sealed using silicone-based tubes for future drug injections.

Example 2

Hydrogel Preparation and Cell Encapsulation Process
Two methods were used to evaluate the long-term viability of the cells in the cross-linked hydrogels and the microchannels. In the first study, OVCAR-8 cancer cells at a density of 10 million cells/mL were encapsulated within the Matrigel®. A 2 μL droplet was embedded in the PEG20K hydrogels, patterned in single-layer disks with dimensions of 160 μm in thickness and 2 mm in diameter. These disks were then cultured in growth media at 37° C. over a period of 14 days. Cell viability was quantitatively evaluated using the MTS assay. Relative cell viability (%) was calculated at days 1, 4, 7, and 14 based on the absorbance readings. Measurements were normalized to day 0 as the control.

In the second study, the viability of encapsulated OVCAR-8 cells in the microfluidic device were tested at three time points (day 4, 7, and 14) through staining with the live/dead assay. This assay identifies esterase activity in live cells via green fluorescence emission from calcein AM and nuclear permeability in dead cells via red fluorescence emission from ethidium homodimer-1. 2×PBS was pumped into the channels to wash out the growth media out. The live/dead staining solution was pumped into the chambers for 5 min at 37° C. The cells were washed with PBS to remove any unbound reagents. A Nikon A1R fluorescence confocal microscope was used to observe the encapsulated cells.

Example 3

Effect of Nanoparticle Morphology and Targeting Agents on Tumor Accumulation

Fluorescently labeled lipid nanoparticles namely (discs, vesicles, discs+folic acid (FA), and vesicles+FA) were diluted individually in phenol-free RPMI-1640 media to a final concentration of 1 mg/mL. Then they were pumped through the chambers by the syringe pump under constant flow conditions for 12 hours, and images were taken using a confocal microscope. A comparison of the fluorescent intensity was performed to observe the effect of the nanoparticle's shape or targeting agents on the accumulation in the tumor.

Example 4

Confocal Microscope Conditions for the Microfluidic Device

The microfluidic device was mounted on a microscope stage inside a 37° C. incubator. Media containing nanoparticles was pumped at a flow rate of 12.96 µL/min, which correlating to the blood flow in tissue capillaries and was controlled using a syringe pump. Images of nanoparticle accumulation was taken using a 40× objectives on a Nikon A1R confocal microscope. Images were taken in the center layer of the 3D tumor every 10 min for 12 hours.

Example 5

Calculating the Rate of NP Accumulation

Fluorescence distribution was analyzed with ImageJ by drawing a contour around the cell aggregates and measuring the mean fluorescence signal at various time points. Tumor accumulation of the nanoparticles was calculated using mean fluorescence in the selected images and normalizing to the fluorescence of the surrounding media. Final calculations were performed by subtracting the background.

Example 6

Characteristic of the Microfluidic Device

The device consists of a main chamber area, with at least two media reservoirs. The main chamber area (10 mm in length×2.2 mm in width×0.160 mm in height was used for tissue culture. The photo-crosslinked gel encapsulating the cells was located between the two rows of the red dots (the PDMS posts with a radius of 100 µm). The function of these posts is to retain the viscous cell-gel solution during loading, giving the cell-gel a definable geometry after photo cross-linking, and to serve as lateral porous supports for the extracellular gel matrix. The device has also been designed for direct observation of 3D cell structures in vitro under controllable flow. The chamber is preferably optically transparent under low or high magnification.

Example 7

Modeling Nanoparticle Drug Carriers in Tumor-On-A-Chip Microfluidic Devices

Figure 8:
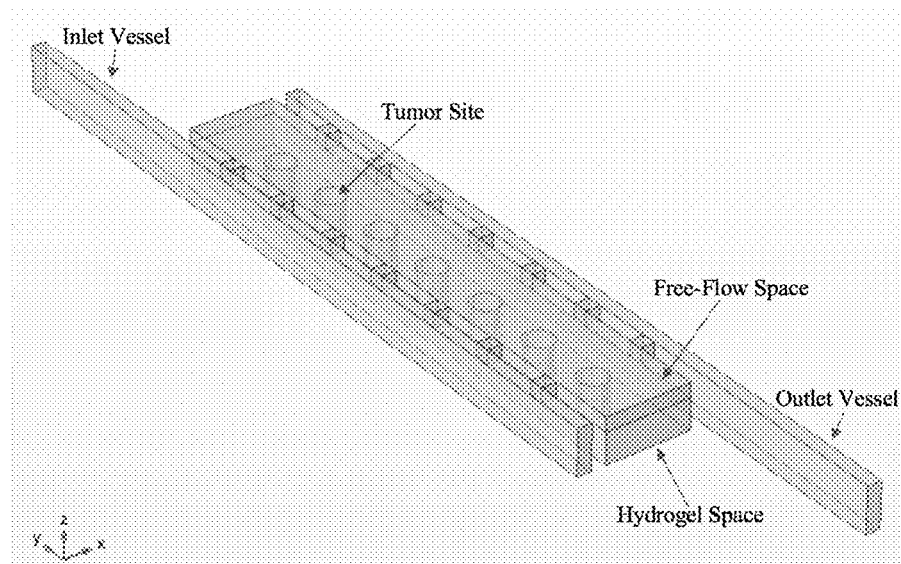
FIG. 8 show a tumor-on-a-chip "N-Shape" design with specified domains.
Figure 9:
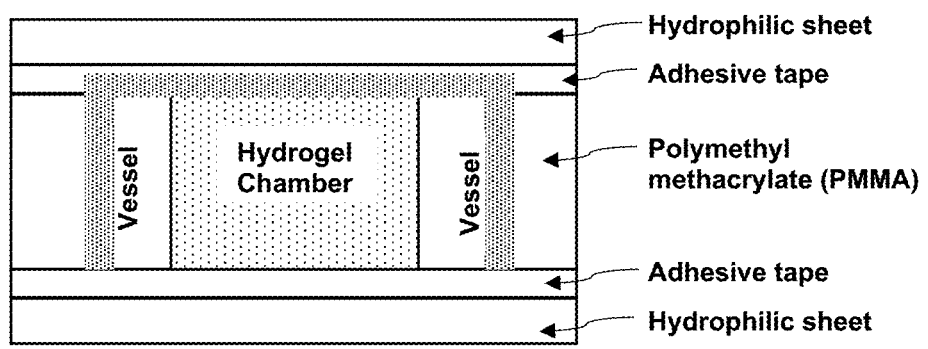
FIG. 9 shows a side view of the tumor-on-a-chip assembly.
Figure 11A:
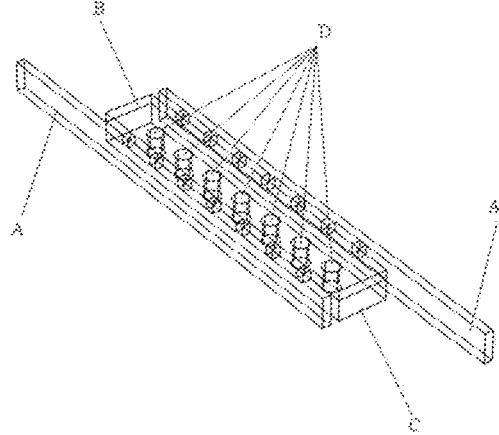
FIG. 11A shows exemplary images of Geometry 1 and FIG. 11B shows Geometry 2. Depicted are the 4 major domains in the 3D model, the flow chamber (A), the free flow space (B), the diffusion chamber (C) and the tumor cells (D).
Figure 11B:
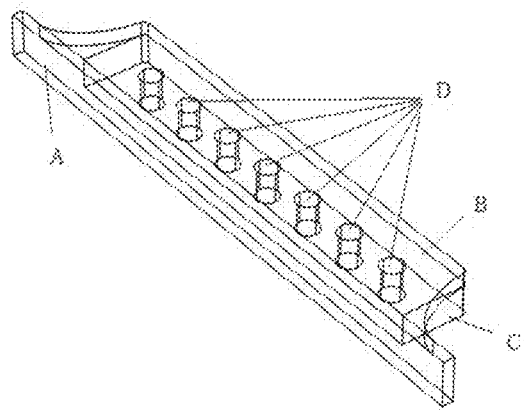
Figure 12A:
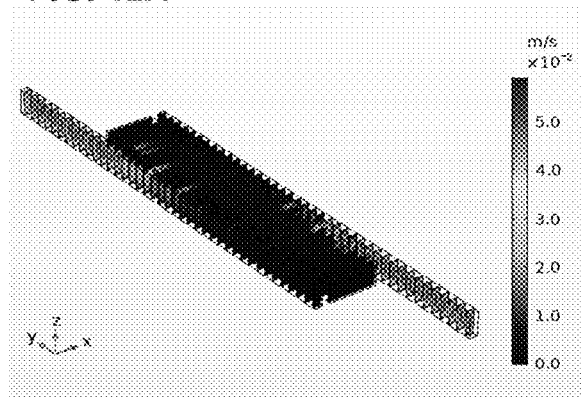
FIG. 12A shows velocity field generated by time independent studies for Geometry 1 and FIG. 12B shows Geometry 2. Velocity is measured in units of mL/sec.
Figure 12B:
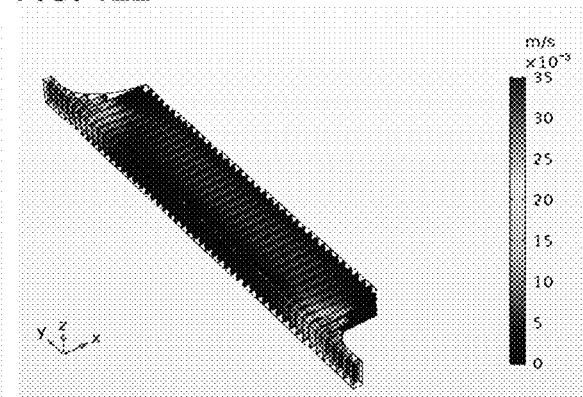
Figure 13A:
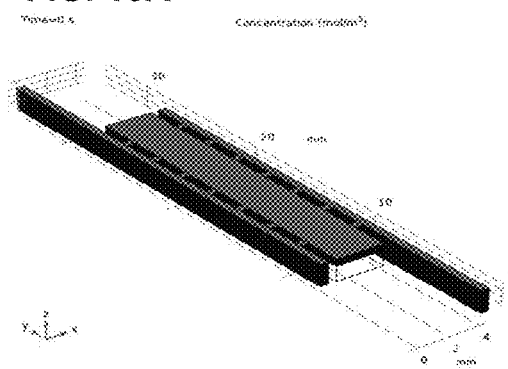
FIG. 13A, t=0.
Figure 13B:
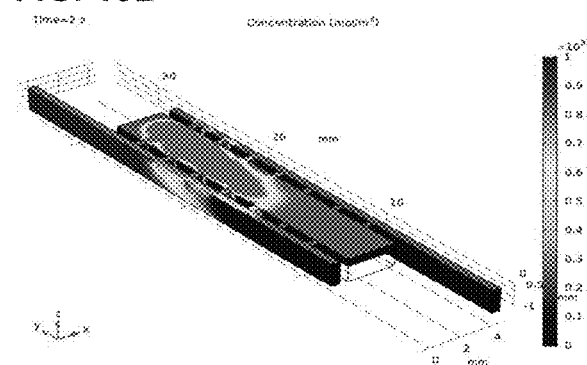
FIG. 13B, t=2 sec.
Figure 13C:
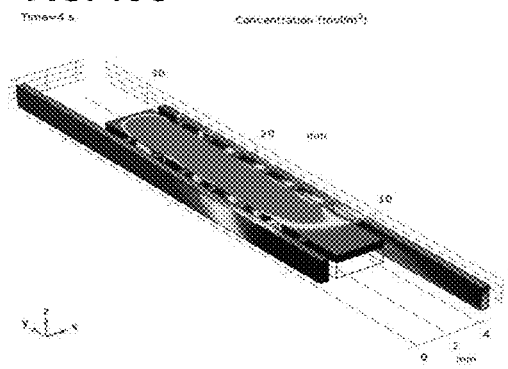
FIG. 13C, t=4 sec.
Figure 13D:
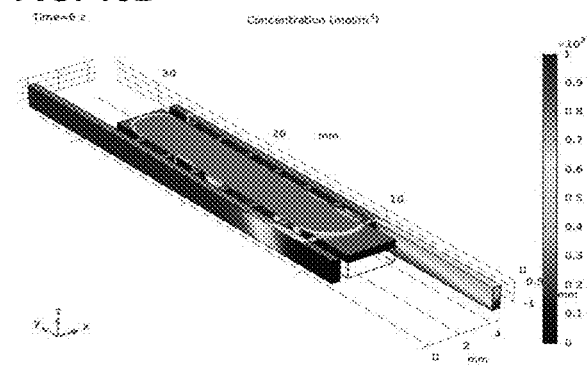
FIG. 13D, t=6 sec. Units for concentrations are in mole/m$^3$ and time values are in seconds.
Figure 14A:
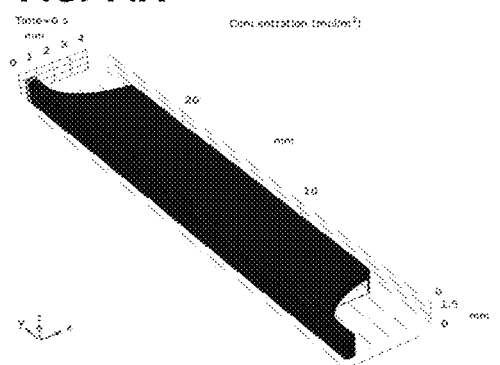
FIG. 14A-D shows concentration n vs. time plots for four different times at 2 second intervals for the flow chambers and free flow domains of Geometry 2.
Figure 14B:
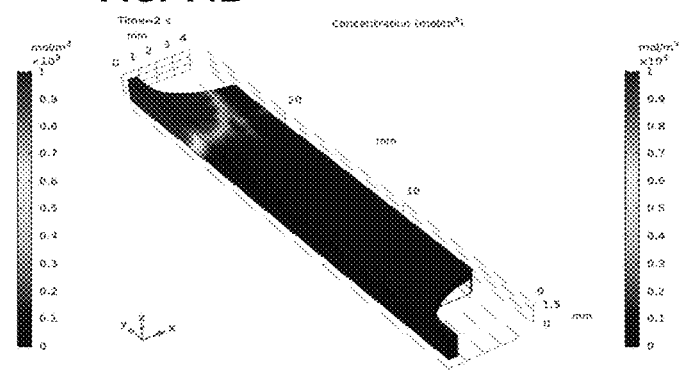
Figure 14C:
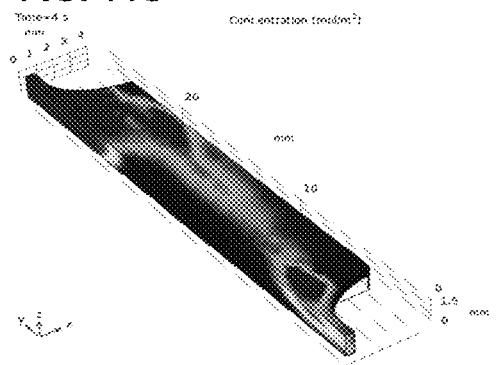
Figure 14D:
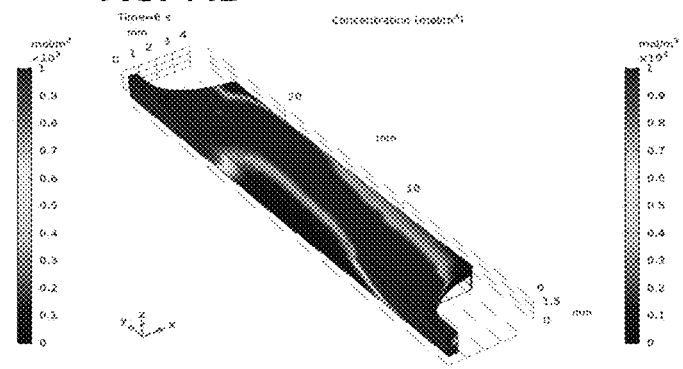
Figure 15A:
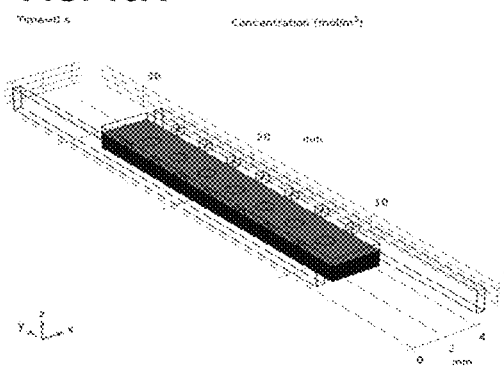
FIG. 15A-D shows concentration n vs. time plots for the diffusion chamber domain of Geometry 1.
Figure 15B:
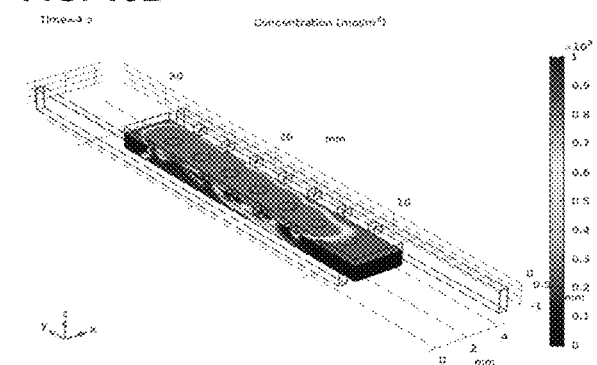
Figure 15C:
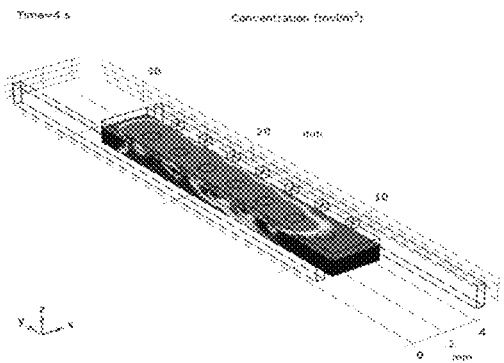
Figure 15D:
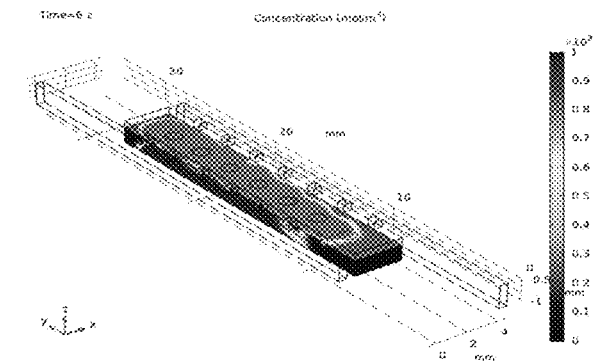
Figure 16A:
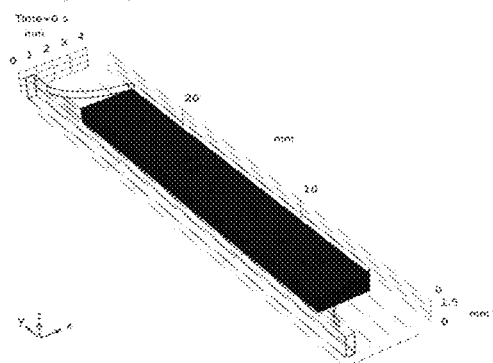
FIG. 16A-D shows concentration vs. time plots for the diffusion chamber domain of Geometry 2.
Figure 16B:
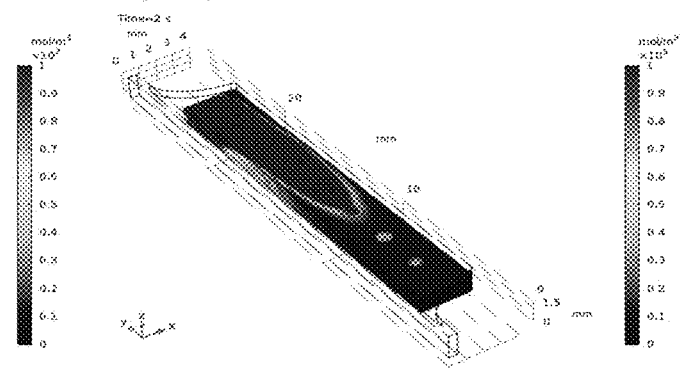
Figure 16C:
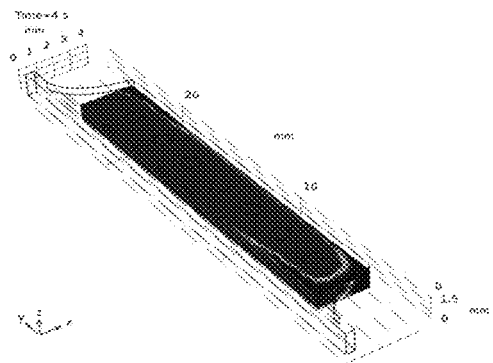
Figure 16D:
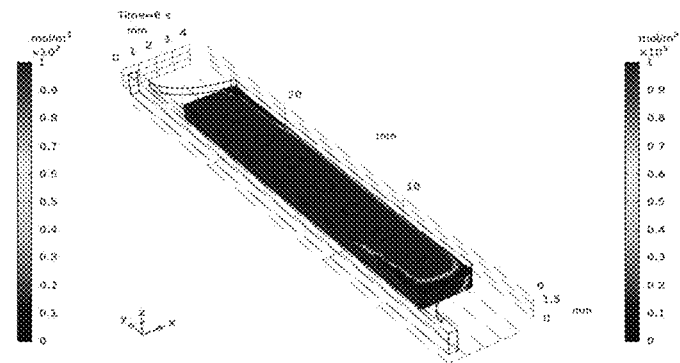
Figure 17A:
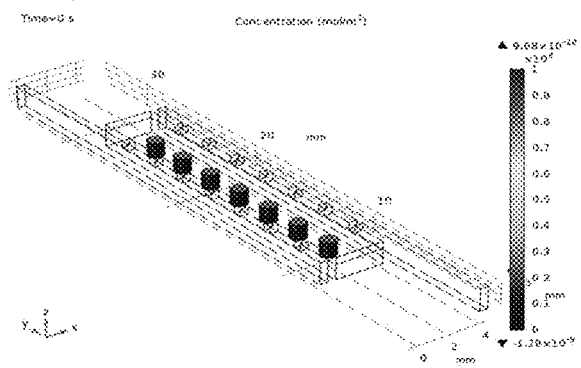
FIG. 17A-D shows concentration vs. time plots for the tumor domain of Geometry 1.
Figure 17B:
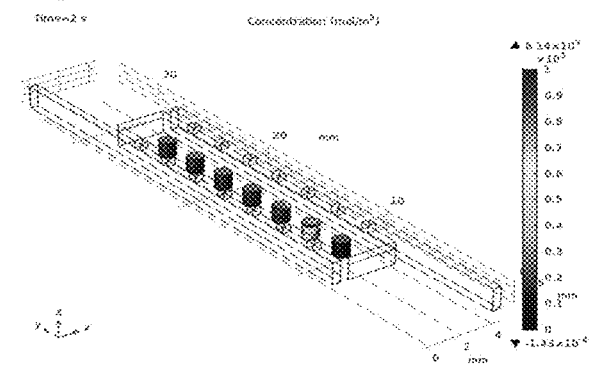
Figure 17C:
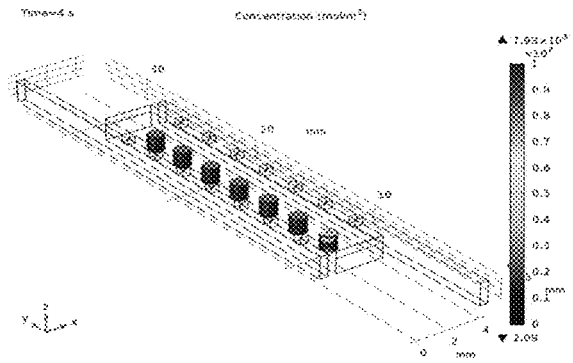
Figure 17D:
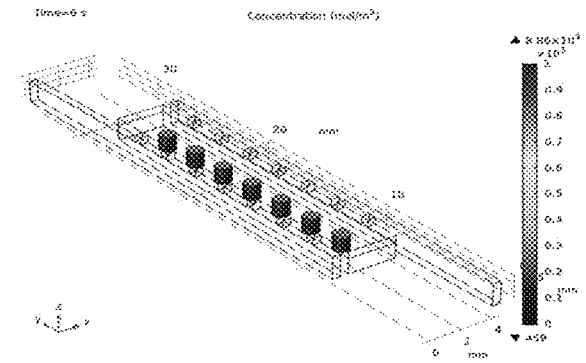
Figure 18A:
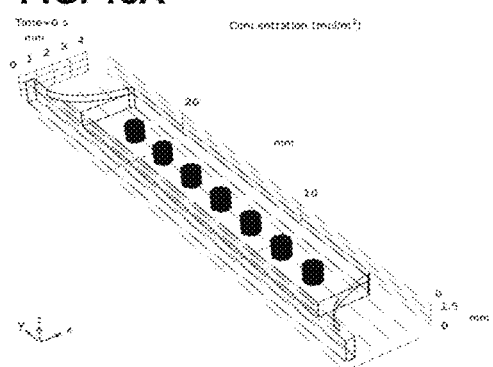
FIG. 18A-D shows concentration vs. time plots for the diffusion chamber domain of Geometry 2.
Figure 18B:
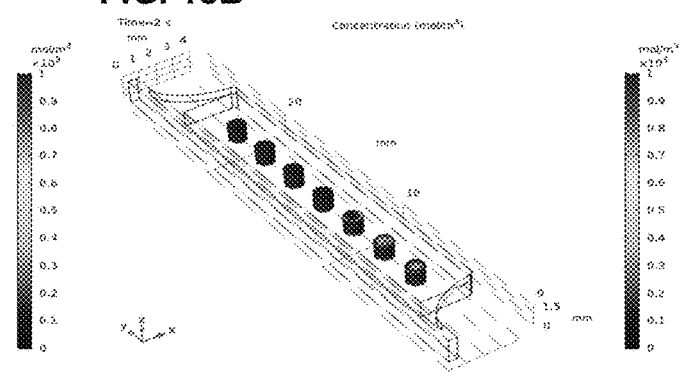
Figure 18C:
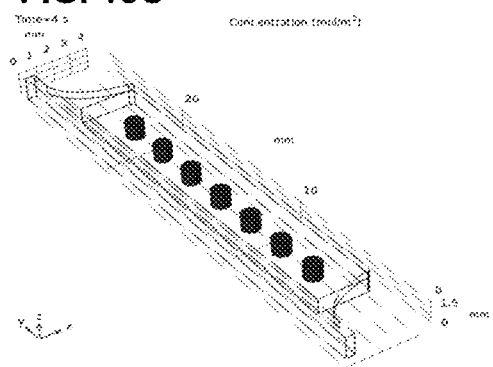
Figure 18D:
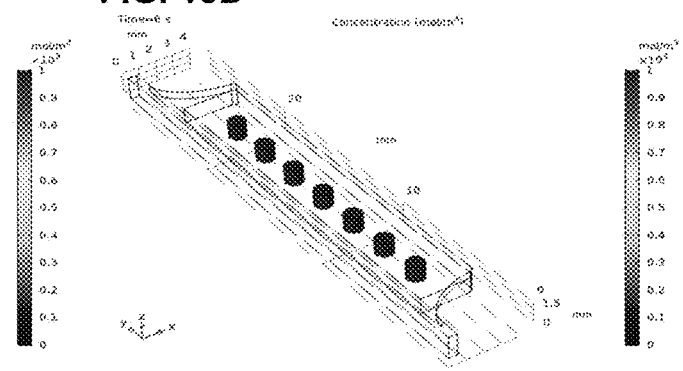

COMSOL Multiphysics® was used to perform simulations of drug diffusion. Two geometries were created for the tumor-on-a-chip designs described herein and the diffusion of cancer drug therapies was simulated. The two geometries are the N-Shape design and the Linear-Shape design. See FIGS. 11A-B. Both geometries contain an inlet and outlet vessel meant to mimic human vasculature and a diffusion chamber. The diffusion chamber domain contains the porous media and a free-flow space above the porous media. The diffusion chamber contains two different porous media domains—the hydrogel and the tumor. One of the geometries is shown below in FIG. 8.

Initial simulations were run using a tracer to mimic the diffusion of low molecular weight drugs. In the simulation using a pulsed tracer, the following parameters were controlled: tracer concentration, inlet flow rate, and the porosity of the porous media. From these simulations, a concentration profile was created that describes the mass transfer of low molecular weight drugs over time. The diffusion of nanoparticles was investigated to determine their accumulation at tumor sites within the tumor-on-a-chip. In addition to controlling the inlet flow rate and the porous medium characteristics, the nanoparticle characteristics were controlled because nanoparticle size and shape are known to affect their accumulation. In these simulations, the size and shape of the nanoparticles were adjusted to determine the optimum conditions for higher accumulation rates. Accumulation rates were determined by the fraction of total accumulated nanoparticles at the tumor sites to the total released nanoparticles. The accumulation rates were used to determine the effects of the nanoparticle characteristics.

Custom materials were created in COMSOL for the hydrogel (agarose) and the tumors by using the porosity parameter. The physics modules used in the COMSOL modeling include: Transport of Diluted Species, Transport of Diluted Species in Porous Media, Laminar Flow, and Particle Tracing for Fluid Flow. The Laminar Flow module calculated a velocity field based on a given normal inlet velocity of tracer. The module also accounts for gravity in its calculations. The Transport of Diluted Species module solved for the convective diffusion of tracer in the vessels and free-flow chambers. The Transport of Diluted Species in Porous Media module calculated the diffusion of the tracer from the top chamber into the two porous media—the hydrogel and the tumor. A Particle Tracing for Fluid Flow module was added. This module models solid particle flow within the device, using given values for particle size, density, and shape. In each simulation, both the tracer and particles followed the velocity field calculated from the Laminar Flow module. This made every module largely dependent on the results produced for the velocity field by the Laminar Flow module.

Both chip designs were tested in COMSOL Multiphysics®. Both a tracer and nanoparticles flowed through the inlet vessel, into the free-flow layer, down into the diffusion chamber, and out through the outlet vessel. Simulations lasted about six seconds, with values being recorded at 0.2 second step increments. Despite the short length of these simulations, the small step size permitted vizualization of how the tracer and nanoparticles diffused over time, while avoiding high computational cost.

In the tracer studies, chip geometry had an impact on the velocity and concentration profiles. This was because the N-Shape model has seven diffusion chambers that limit the flow of tracer from the vessel into the free flow domain, while the Linear-Shape design is open between the vessel and the free flow domain.

In order to verify the simulated tracer results, the observations and animations from COMSOL were compared to video footage of a laboratory experiment. This experimental work was done only using the N-Shape design. Food coloring was used to imitate the tracer flowing through a tumor-on-a-chip, and to visualize the tracer diffusion patterns. The experimental videos confirmed the simulated flow path of tracer from COMSOL.

The COMSOL simulation also allowed investigation of the impact of size and shape of nanoparticles on tumor-site specific particle accumulation. Sizes varied from 0.1 nm to 5000 nm and were representative of drug types from small-molecule drugs (hydrocarbons) to microparticles (lipids). The shapes of the nanoparticles were modified from a standard sphere to a flattened disc or rod by using the sphericity parameter available in the Particle Tracing for Fluid Flow module. Sphericity only accounts for the ratio of surface area of a given shape compared to the surface area of a sphere with the same volume rather than actual particle geometry. Because of this, no trends associated with changing particle shape were observed.

The nanoparticle studies showed that neither particle size nor shape had a significant impact on tumor-site accumulation. This was likely due to COMSOL's limitations with respect to porous material creation. Only porosity could be specified, and pore size could not be accounted for, which was not ideal. Chip geometry did impact particle accumulation, with the N-Shape model showing higher accumulation than the Linear-Shape model.

Description of Design Solution

COMSOL Multiphysics® Model Description

The basis for each COMSOL simulation was the geometry used. One model represents the N-shape chip (Geometry 1) shown in FIG. 11A, and one model represents the linear shaped chip (Geometry 2), shown in FIG. 11B. The geometries are two interpretations of how the tumor microenvironment could be represented in a microfluidic device.

The flow chamber domains in the 3D geometries represent the space where liquid enters and exits the tumor-on-a-chip. This domain of the microfluidic device represents the blood vessel pumping blood into the nutrients of a tumor. The domain contains the entry and exit flows for fluids and particles moving through the chip, and in both geometries, the flow chambers connect directly to the free flow space.

The free flow space domains in the 3D geometries represent the space above the hydrogel in the tumor-on-a-chip. This space within the microfluidic device stands in for a specific portion of the blood vessel; the area in the blood vessel positioned directly adjacent to the tumor. This area is the point of entry for blood, drugs, and nanoparticles flowing into the tumor. The area acts as a boundary between the blood vessel and the tumor's extracellular matrix. Because of this boundary, the free flow space shares a boundary with the diffusion chamber in the 3D model.

The diffusion chamber domain lies directly below the free flow space domain. This rectangular region portion of the 3D model represents the portion of the tumor-on-a-chip consisting of the hydrogel surrounding the tumor cells. Hydrogels are an integral part of the tumor-on-a-chip; their properties are very similar to that of the extracellular matrix surrounding the cancer cells. The specific hydrogel chosen for these experiments was agarose gel. Nanoparticles and blood entering from the bloodstream are impeded by the fact that they must diffuse through the denser extracellular matrix, but once the nanoparticles have diffused through, they enter the tumor cell region.

Figure 10A:
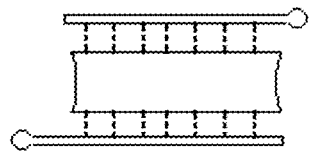
FIG. 10A shows the cross-sectional views of an N-Shape chip.
Figure 10B:
FIG. 10B shows a Linear-Shape chip.

The 6 cylindrical regions are the tumor cell domain. These domains are the "tumor" in the "tumor-in-a-chip." The cylindrical regions are spaced evenly apart, and their heights span from the bottom of the diffusion chamber to the free flow space. Both 3D models share the 4 core domains, but several notable differences can be observed. FIG. 10A-B.

The largest difference is how the flow chamber domains are assorted about the free flow and diffusion chamber domains. In Geometry 1 the flow chambers are attached to both sides of the free flow and diffusion chamber domains. This forces the fluid flow to travel from the flow chamber containing the inlet, into the free flow chamber above the hydrogel. What does not diffuse downward must exit out through the flow chamber containing the outlet on the opposite side. In Geometry 2 the inlet and outlet are on the opposite side of the same flow chamber. In contrast to Geometry 1, the free flow domain is positioned adjacent to the flow chamber; rather than having fluid directed through 6 tiny slit-like chambers on both sides of the diffusion chamber, Geometry 2 has a free flow domain with no barriers between it and the flow chamber. Fluid can flow openly between the two domains with no obstruction. Both of these variations represent a different simplification of tumor microenvironment. The variations were included to add variety to the data set, and to try modeling with a microfluidic device geometry that hadn't yet been popularized. Another difference would be that of the corners of the diffusion chamber and free flow domains. In Geometry 1, the edges of the diffusion chamber and the free flow region are right angles. In Geometry 2, they are rounded out. This variation was an attempt to prevent bubble formation within the chip, as it was a large problem encountered while gathering data in the lab.

To simulate drug diffusion, COMSOL requires that the materials allowed in a given domain be specified. Within the COMSOL interface, a material must be defined, or chosen from a list of preset materials. Properties of various materials are listed in Table 1.

TABLE 1

Material properties used in simulation at standard temperature and pressure

| Material | Dynamic Viscosity (Pa · s) | Density (kg/m$^3$) | Porosity |
| --- | --- | --- | --- |
| Water | $8.9 \times 10^{-4}$ | 997.77 | —* |
| Hydrogel | $8.9 \times 10^{-4}$ | 1640 | 0.5 |
| Tumor | $8.9 \times 10^{-4}$ | 1640 | 0.1 |

*Porosity values were not included for water because water is not a porous medium.

The only material whose properties are already available in COMSOL's presets was water. It was assumed that the chip was fully saturated with water prior to the pulse of tracer. Therefore, every domain was specified to have water for the tracer analysis. The flow chamber and free flow domains are empty at the beginning of the simulation, and as the simulation progresses, tracer enters through the device's inlet, is able to diffuse into the chamber containing the hydrogel and exits through its outlet. The second material is the agarose stored in the diffusion chamber. COMSOL has no tabulated data on agarose, so the inputs needed to be manually inserted. This allowed the simulation to model drug diffusion based on relevant physical properties of the agarose. Once the tracer diffuses through the agarose, it then diffuses through the tumor cells. A "Tumor" had to be defined material to accurately model tracer diffusion into the tumor cells domains.

COMSOL's greatest strength as a simulation software is its Multiphysics® Tool. With COMSOL Multiphysics®, multiple physics modules can be utilized simultaneously, which allows for the governing equations of any physics module to interact with the equations of another module in a given simulation. The physics integral to this simulation were Laminar Flow, Transport of Diluted Species, Transport of Diluted Species in Porous Medium, and Particle Tracing in a Fluid.

The Reynolds number was used to determine whether the flow within the chip was laminar:

$$Re = \rho u d/\mu \quad \text{(Equation 1)},$$

where $\rho$ represents the density of the fluid, variable u represents the fluid's normal velocity, d represents the diameter of the tube or pipe the fluid is moving through, and $\mu$ represents the fluid's dynamic viscosity.

The normal inlet velocity in the chip was calculated using the cross-sectional area of the flow chamber from a known inlet volumetric flow rate used during experimental testing. The normal inlet velocity was found to be 0.033 m/s. If standard temperature and pressure are assumed, the dynamic viscosity of and density would equal $8.9 \times 10^{-4}$ Pas and 997.77 kg/m$^3$, respectively, resulting in a Reynolds number of 18.5. This is far below the upper limit of 2100, so the flow moving through the chip is laminar.

With the Laminar Flow interface, particle movement is governed by the simultaneous solving of the Navier-Stokes Equation with the Continuity Equation:

$$\underbrace{\rho\left(\frac{\partial u}{\partial t} + u \cdot \nabla u\right)}_{1} = \underbrace{-\nabla p}_{2} + \underbrace{\nabla \cdot \left(\mu(\nabla u + (\nabla u)^T) - \frac{2}{3}\mu(\nabla \cdot u)I\right)}_{3} + \underbrace{F}_{4} \quad \text{(Equation 2)}$$

$$\frac{\partial \rho}{\partial t} + \nabla \cdot (\rho u) = 0, \quad \text{(Equation 3)}$$

where u is the velocity field, p is fluid pressure, and $\rho$ represents fluid density, and 1 represents the identity tensor for the shear stress being experienced by the fluid. Navier-Stokes considers the conservation of momentum, and each term represents the forces applied internally and externally on the fluid. Term 1 represents inertial forces, term 2 represents forces coming from pressure, term 3 represents all the viscous forces in the fluid, and term 4 stands in for any external forces being applied on the fluid. Equation 3 is derived from the laws of mass conservation. Using these two equations and known values from the boundary conditions at the inlet, COMSOL solves for the velocity profile of the fluid flowing through the flow chamber and the free flow domains for each finite element in the 3D mode. In this case, the flow is assumed to be incompressible, and that it does not vary with time.

The Transport of Diluted Species Physics was used to map a concentration profile for tracer in the flow chamber and free flow domains. Using this Physics interface, the main equation dictating the movement is Fick's Law with an additional convection term:

$$N_i = -D_i \nabla C_i + C_i u; \quad \text{(Equation 4)}$$

$$\frac{\partial C_i}{\partial t} + \nabla \cdot N_i = R_i, \quad \text{(Equation 5)}$$

where $N_i$ is the molar flux vector of a species, $D_i$ is the diffusivity coefficient of a species i in a solute, $C_i$ is the concentration of a given species i, u represents the velocity field at a specific point where movement by species i is being measured, the partial derivative of ci with respect to time is the change in concentration with respect to time at a given position, and $R_i$ is a term incorporating any generation or consumption of species i throughout the process.

While diffusion takes into account tracer movement due to a concentration gradient between the inlet and the outlet, a term for convection must be included to incorporate the effects of bulk fluid movement on tracer movement. Diffusion is generally a slow process and is likely eclipsed by the impact the velocity field has on the movement of the tracer throughout the chip. Since there are no reactions occurring within the chip, none of the tracer is being consumed or generated, so the $R_i$ term can be ignored. This suggests that the movement of the tracer throughout the flow chamber and free flow domains are almost solely influenced by convective forces.

To measure how the concentration moves through the hydrogel in the diffusion chamber domain, and through the tumor cells themselves, both the hydrogel and tumor cells were treated as porous media. The diffusion of the tracer through these domains was simulated with The Transport of Diluted Species in Porous Media Physics. The equations used by COMSOL to model dilute species traveling through porous media at relatively low velocities are as follows:

$$\nabla \cdot N_i + u \cdot \nabla C_i = R_i; \quad \text{(Equation 6)}$$

$$N_i = -D_{e,i} \nabla C_i; \quad \text{(Equation 7)}$$

$$D_{e,i} = \left(\frac{\varepsilon_p}{\tau_{F,i}}\right) \cdot D_{F,i}; \quad \text{(Equation 8)}$$

$$\tau_{F,i} = \varepsilon_p^{-\frac{1}{2}}, \quad \text{(Equation 9)}$$

where $N_i$ represents the molar flux vector of species i, u is the velocity field vector at a given point, ci is concentration of species i, and $R_i$ is the amount of species i consumed or generated in a reaction, which will once again be zero since there is no reaction. $D_{e,i}$ is the diffusivity coefficient in porous media, $D_{F,i}$ is the diffusivity coefficient when the diluted species is diffusing solely through its solvent, $\varepsilon_p$ is the porosity of the porous medium, $\tau_{F,i}$ is the tortuosity of the porous medium with respect to species i.

Equation 6 and Equation 7 take into account both the convective and the diffusive forces impacting the tracer's migration through the porous medium. The molar flux of species i, $N_i$, undergoes a slight change in definition from prior equations, as the molar flux of species i is now dependent on the diffusion coefficient in the porous medium, $D_{e,i}$. The new coefficient for diffusion depends on the porous medium's porosity $\varepsilon_p$, the tortuosity of the porous medium $\tau_{F,i}$, and the diffusion coefficient of the solute in just the solvent $D_{F,i}$. The Transport of Diluted Species in Porous Media interface can also be set to use the Bruggerman model to relate medium tortuosity with medium porosity, as shown in Equation 9.

To simulate nanoparticles moving through the microfluidic device, the Particle Tracing Multiphysics was used. With the Particle Tracing Physics, particle movement is dictated by the force applied to particles by a velocity field.

$$F_t = \frac{d(m_p v)}{dt}. \quad \text{(Equation 10)}$$

The force applied to the particle is modeled using Equation 10. $F_t$ represents the force vector being applied to a particle, $m_p$ is the mass of said particle, and v, the velocity of the particle.

Because nanoparticles moving through a microfluidic device will experience a sizable amount of drag, COMSOL includes an equation to incorporate the effect of drag force on the particles. Because nanoparticles of varying shape were used, the Haider-Levenspiel correlation was used to calculate drag force. COMSOL used the following equations in the model:

$$F_D = \left(\frac{m_p}{\tau_p}\right)(u - v); \quad \text{(Equation 11)}$$

$$\tau_p = \frac{(4\rho_p d_p^2)}{(3\mu C_d R_{e_r})}; \quad \text{(Equation 12)}$$

$$R_{e_r} = \rho|u - v|\frac{d_p}{\mu}; \quad \text{(Equation 13)}$$

$$C_D = \frac{24}{R_{e_i}} \cdot [1 + AR_{e_r}^B] + \frac{C}{\left(1 + \frac{D}{R_e}\right)}. \quad \text{(Equation 14)}$$

Equation 11 shows how to calculate the drag force vector $F_D$. The vector is defined by the difference between vectors u and v, the velocity of the bulk fluid and the particle, respectively. The magnitude of the vector is then directly proportional to the mass of the particle, mp, and the inversely proportional to the shear stress experienced by the particle, $\tau_p$.

The Physics interface calculates shear stress using Equation 12. Shear stress experienced by the particle is directly proportional to product of the density of the particle, $\rho_p$, and the square of the particle's diameter, $d_p$, and inversely proportional to the dynamic viscosity of the fluid, $\mu$, the particle Reynolds number, $R_{e_r}$, and the drag coefficient $C_D$.

COMSOL calculates the particle Reynolds number similarly to how it calculates Reynolds number used for flow through a pipe or tube. There are, however, two notable differences: rather than using the velocity of the bulk fluid, COMSOL uses the magnitude of the difference between the bulk fluid velocity vector and the particle velocity, and rather than using the diameter of the tube, COMSOL uses the particle diameter in its calculation.

The Haider-Levenspiel correlation was chosen for the drag coefficient, Equation 14, for this simulation. The correlation uses both the particle Reynolds number alongside the coefficient A, B, C and D to calculate the drag coefficient. These 4 coefficients are all functions of the particle's sphericity and allows for changes made to the shape of the nanoparticles flowing through the microfluidic device to be taken into account by the COMSOL simulation.

Tracer Analysis

One of the focuses for this project was to determine COMSOL's capability of modeling the diffusion of low-molecular weight drugs within the tumor-on-a-chip. The simulation ran a tracer through both Geometries 1 and 2 and measured the concentration profiles observed in each of the domains. To model tracer diffusion, the Laminar Flow, Transport of Dilute Species, and Transport of Diluted Species, and the Transport of Diluted Species in Porous Media were used.

The first necessary step was to use the Laminar Flow Physics module to generate a velocity field between the inlet and outlet of the microfluidic devices. Without a velocity field to direct the tracer, the Transport of Diluted Species and Transport of Diluted Species in Porous Media interfaces only take into account diffusive movement of the tracer within the tumor-on-a-chip, and does not accurately represent the tracer's movement through the device.

The tangential inflow for the tracer was set to the inflow calculated for the Reynolds number calculations earlier, 0.033 m/s. No-slip boundary conditions were set for every exterior wall of both geometries. The temperature and pressure were set 25° C. and 1 atm respectively, and a time-independent simulation was run to calculate the velocity field.

The geometries had clear impacts on the velocity field. In Geometry 1, flow is constricted at the 7 tiny slit-like chambers leading both into, and out of, the diffusion chamber domain. Higher velocities were observed in the first 3 slits entering the diffusion chamber from the top left of the diffusion chamber, and the last 3 slits on the bottom right of it. In contrast, due to the uninterrupted opening between the flow chamber and the free flow space domains in Geometry 2, the velocity field shows an increase in velocity in a bell-shaped curve spanning both the flow chamber and free flow space domains, before increasing sharply right before reaching the exit.

A concentration profile was calculated that measured tracer diffusion throughout the chip. COMSOL calculated the concentration profile using the velocity fields from the time-independent study, and the Transport of Diluted Species and Transport of Diluted Species in Porous Media physics modules.

To initiate the simulation the following parameters were chosen: inlet concentrations were arbitrarily set to 1000 gram-moles per cubic meter so that tracer concentration could still be considered diluted, and initial values for the tracer concentration were set to zero throughout the device. The diffusion chamber and tumor cells were marked as a porous media, and the domains were filled with the hydrogel and tumor materials. The properties of these materials relevant to the two Physics interfaces used to make the concentration profiles are described in Table 1. No-flux conditions were set for the exterior walls for both geometries to make sure the tracer diffuses only within the chip. Boundaries between the free flow space, diffusion chamber, and tumor domains calculated diffusion between domains using concentration profiles calculated at boundary surfaces. A time-dependent study was then run to calculate the concentration profiles for the tumor domains over time.

FIGS. 12-18 show the progression of the tracer's diffusion into Geometry 1 and 2. Each panel shows discrete time-points of tracer concentration over a time span of 6 seconds, starting at 0 seconds, and increasing in intervals of 2 seconds. These figures all show that the tracer concentration profile predictably follows the velocity fields generated in FIG. 12, demonstrating the impact of the convective forces on tracer diffusion.

Both FIGS. 13 and 14 best confirm the resemblance between the velocity profile and concentration profiles for both geometries. In Geometry 1, the tracer follows along the path laid out by the velocity field in the N-shape chip, and in Geometry 2 the concentration profile follows the same bell-shaped curve defined by its velocity profile.

This flow path, however, has consequences on the diffusion into the domains below. The tracer diffuses more slowly in the last tumor cells in Geometry 1, because of the positioning of the slits connecting the free flow space domain to the flow chamber domain. In Geometry 2, the tracer covers almost the entirety of the free flow space above the diffusion chamber domain. This can be seen in FIGS. 15 and 16, where the tracer has much higher concentrations in more of the diffusion chamber in Geometry 2 at a time of 6 seconds than 1, and that much of the tracer did not diffuse past the slits at the end of the chamber. This was much more conducive to the migration of the tracer into every tumor cell. This can be seen in FIGS. 17 and 18, where higher concentrations of tracer can be seen more quickly in the tumor cells furthest from the inlet in Geometry 2 than can be seen in Geometry 1.

Example 8

Sample Tissue Preparation

Figure 19:
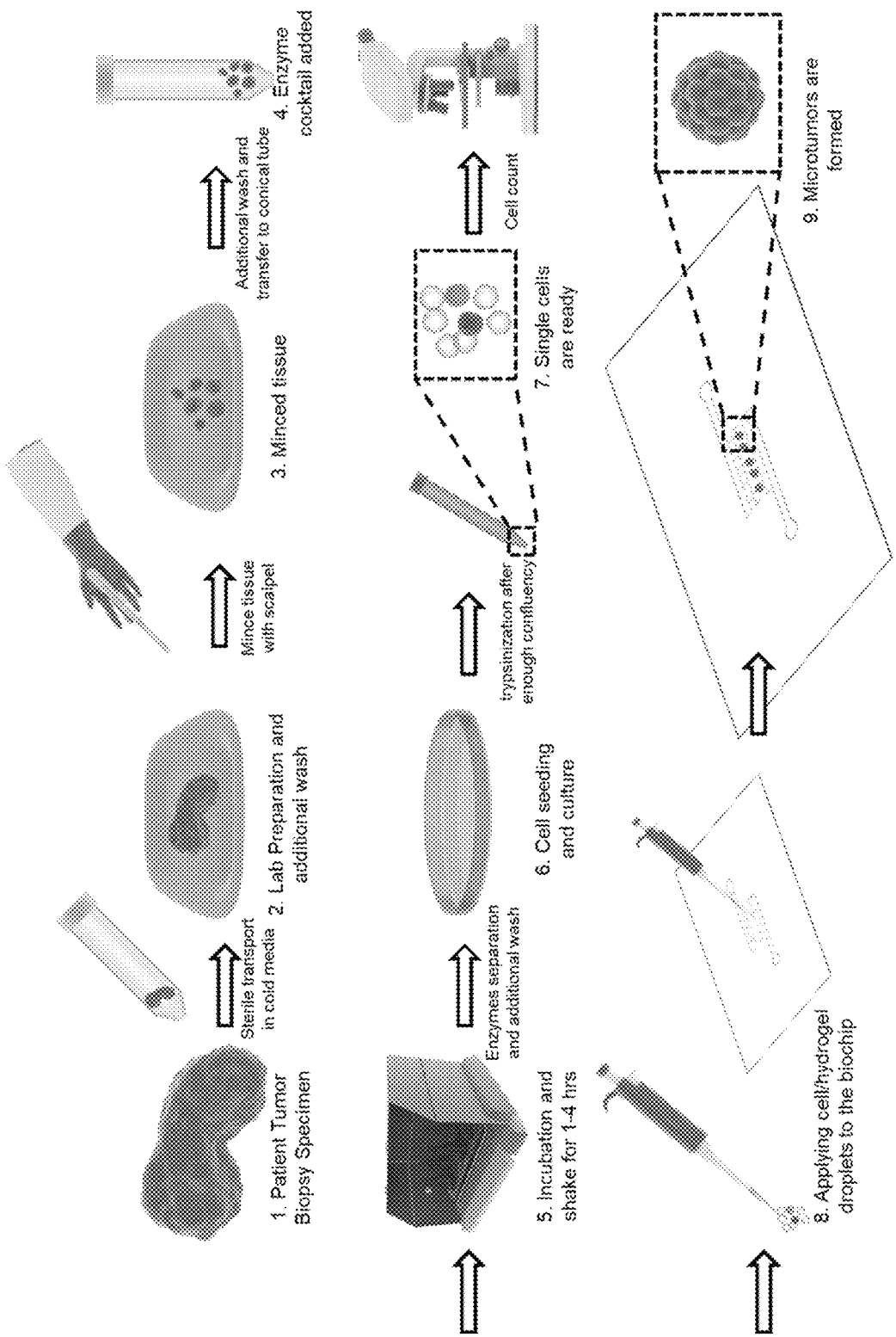
FIG. 19 shows a step-by-step illustration of tissue dissociation protocol. Surgically resected patient samples will be transported in PBS or media (cold temperature). Mechanical dissociation will be followed by enzymatic dissociation using an optimized enzymatic cocktail. Ammonium-Chloride-Potassium (ACK) lysis can be used to eliminate contamination.
Figure 20:
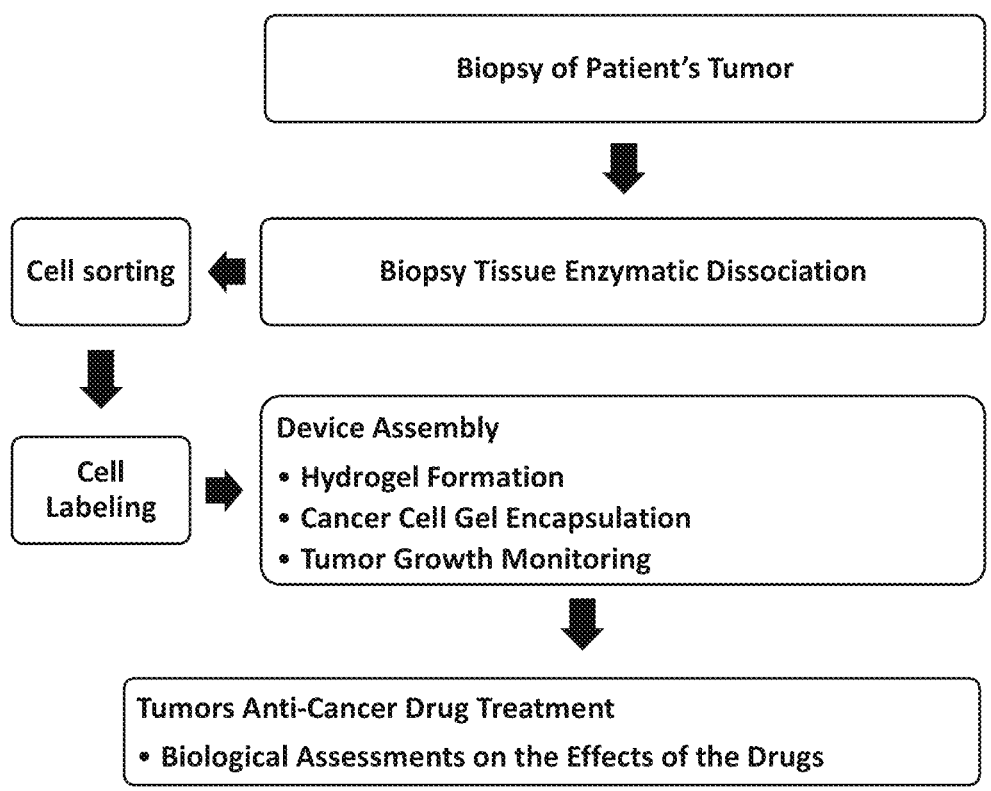
FIG. 20 shows an exemplary flowchart of the analysis procedure.

For the preparation of single cells from tissues from surgical resections, samples should be placed in an appropriate medium. The volume of media or normal saline should be enough to immerse the entire sample (FIG. 19). Ideally, samples should be transported directly to the laboratory for preparation at 4° C. temperature. Surgical tissue sample pieces should be transported from the operating room on ice in sterile specimen cups in DMEM/F12/H supplemented with 5% FBS. The size of the specimen container will depend on the amount of tissue; typically, a 5 mL vial was used. Upon delivery to the laboratory, the tissue was transferred in a vertical laminar airflow hood to sterile Petri dishes and further minced with scalpels. Large lobes of parenchymal tissue were trimmed at this time. The transfer medium typically was DMEM/F12/H supplemented with 5% FBS, on ice. Media can be modified depending on the type of the tumor, as different cell types may have distinct nutrient and supplement requirements. Furthermore, if additional assays, such as a signaling response assay using phospho-specific flow cytometry need to be performed, further modification on the medium ingredients will be applied (e.g., growth factor supplements). Generally, these combinations may be used:
  a. Solid Tumor: DMEM/F12+Glutamax (Life Technologies, MA) with a defined hormone and salt mix and 50 µg/mL gentamicin sulfate (Corning, N.Y.).
  b. Skin: DMEM (Corning, N.Y.) with 10% FBS (Thermo Fisher Scientific, MA)+100 units/mL Penicillin and 100 µg/mL streptomycin (GE Healthcare, PA).
  c. Blood: RPMI 1640 (Corning, N.Y.) with 10% FBS (Thermo Fisher Scientific, MA)+1×100 units/mL Penicillin and 100 µg/mL streptomycin (GE Healthcare, Pittsburgh, Pa.).

Upon receipt, samples were transferred to 50 mL conical tubes and centrifuged at 100×g at room temperature for 3 min to pellet cells and tissue pieces. The supernatant was discarded by pipetting and resuspend tissue in 5 mL of 37° C. medium. Larger tissues (larger than 1 cm$^3$) requires additional mincing. Dead cells do not pellet effectively at 100×g and will be contained in the supernatant with other, non-cellular tissue components and secreted factors. Tissue and media were then transferred into a 60 mm petri dish. Using a scalpel, tissues were gently minced into ~1-2 mm$^3$ pieces. Minced tissue and cells were then transferred into 15 mL conical tubes. Another round of centrifugation was performed at 100×g at room temperature for 5 min. The supernatant was discarded by pipetting, and 4.5 mL fresh medium at 37° C. was added per ~1 mm$^3$ of tissue. About 300-500 µL of an enzyme cocktail was added to the samples. The cocktail ingredients can be modified depending on the type of the tumor. One cocktail contained a mixture of collagenase II (final conc. of 1 mg/mL) and DNase I (final conc. 100,000 U/mL). An alternative cocktail contains a combination of collagenase (final conc. of 300 U/mL) and hyaluronidase (final conc. of 100 U/mL). The dissociation flasks were then sealed and placed on a rotary shaker in a 37° C. incubator. Using a rotary shaker, depending on the tissue type and enzyme concentration, the dissociation may take place 10 minutes to 16 h. Longer dissociation times are required in fibrous tumor samples. Using 10 mL plastic or siliconized glass serological pipet, fragments of tissue that have not undergone complete digestion will be separated for the second round of digestion with collagenase and hyaluronidase. After trituration (pipette 25-50 times) the cell suspension should look homogeneous and have no visible tissue pieces. If needed, samples can be strained with a 70 µm cell strainer, and after an additional washing step, followed by centrifugation at 100×g at room temperature for 10 min. Samples can be used for further studies.

To separate the cells further, the centrifuged cell pellet can be resuspended in 5 mL or more of warm media and centrifuged at 100×g at room temperature for 10 min; the supernatant is discarded. The dissociated tissue was transferred to 15-mL centrifuge tubes and centrifuged for 30 s at 80×g. After removal of the supernatant, the pellet (the "A" pellet) is highly enriched for epithelial organoids. If the supernatant is transferred to a new 50-mL centrifuge tube and centrifuged at 200×g for 4 min, a second pellet (the "B" pellet) is obtained that contains variable numbers of epithelial cells, stromal cells, and red blood cells. The supernatant from this second centrifugation is particularly enriched for human mammary fibroblasts (and their precursors). These latter cells were collected by transferring the supernatant to a third 50-mL centrifuge tube and harvesting the pellet obtained after centrifugation at 450×g for 5 min. Cells can then be injected into the biochips and be grown for up to 21 days. The in situ and post-treatment studies can be performed depending on the design of the experiment.

Example 9

Evaluation of Cell Aggregation in the Hydrogel

Figure 21:
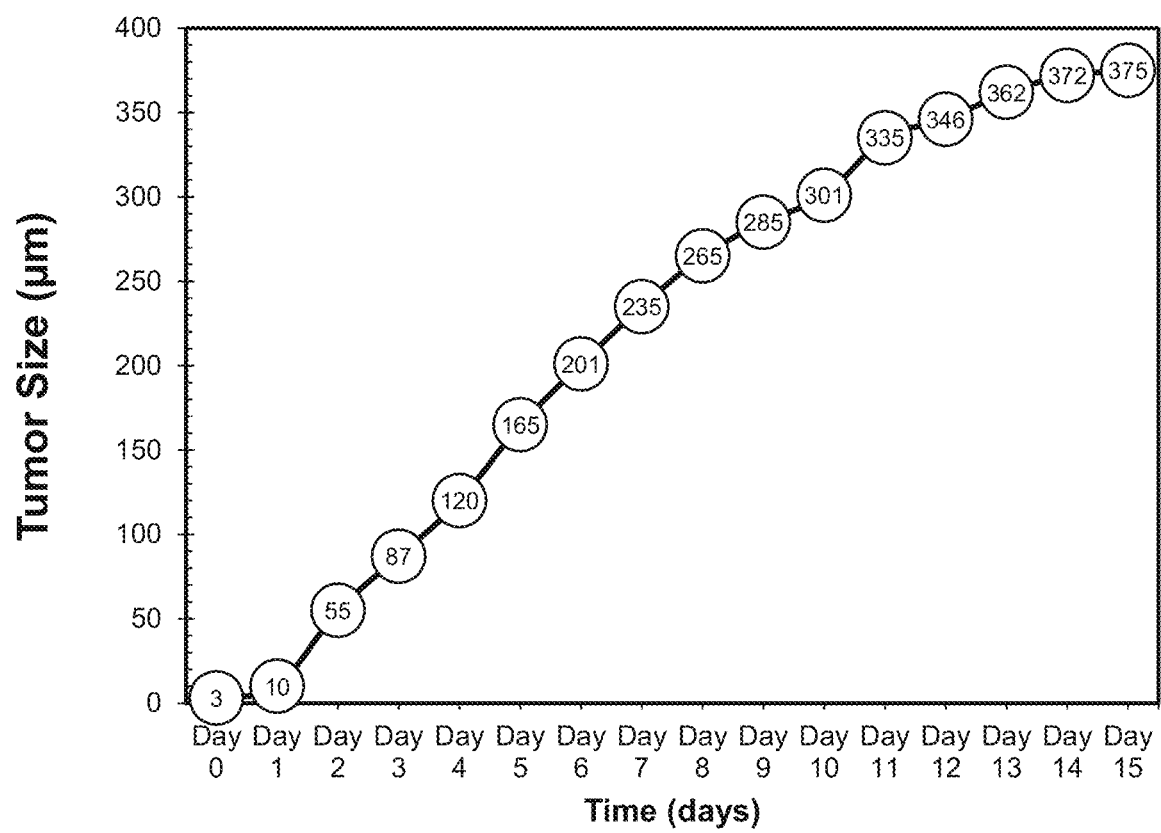
FIG. 21 shows microtumor growth in the microfluidic chips. The size of the OVCAR-8 cell aggregates in PEG 20K hydrogels was measured and monitored over 14 days.

To evaluate the growth of OVCAR-8 cells inside the microfluidic devices, several images were taken with a Zeiss Axiovert 40 CFL inverted microscope at several time points starting from day 0 up to day 14. Images were analyzed in ImageJ to monitor tumor formation by measuring the diameter of each aggregate. Results (FIG. 21) indicate that OVCAR-8 cells begin to form small aggregates after 48 hours of encapsulation and grow to ~235 µm in length by day 7.

Example 10

Cell Viability

Figure 22:
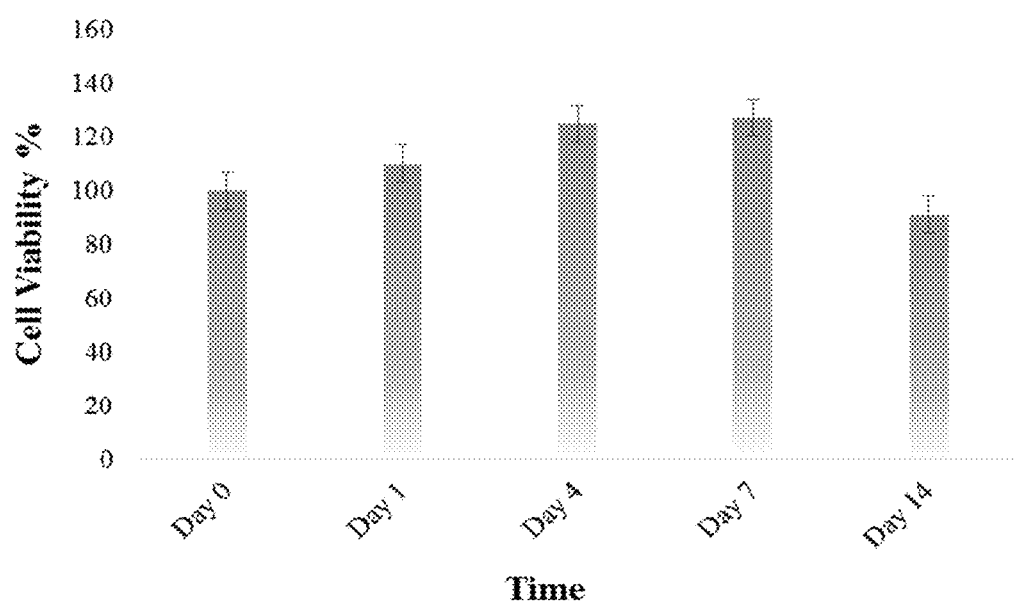
FIG. 22 shows OVCAR-8 cell growth and viability over 14 days in PEG 20K hydrogels. The absorbance readings at 490 nm were normalized to day 0, to reflect the growth of the cells. All values are the mean±standard deviation (n=3).
Figure 23:
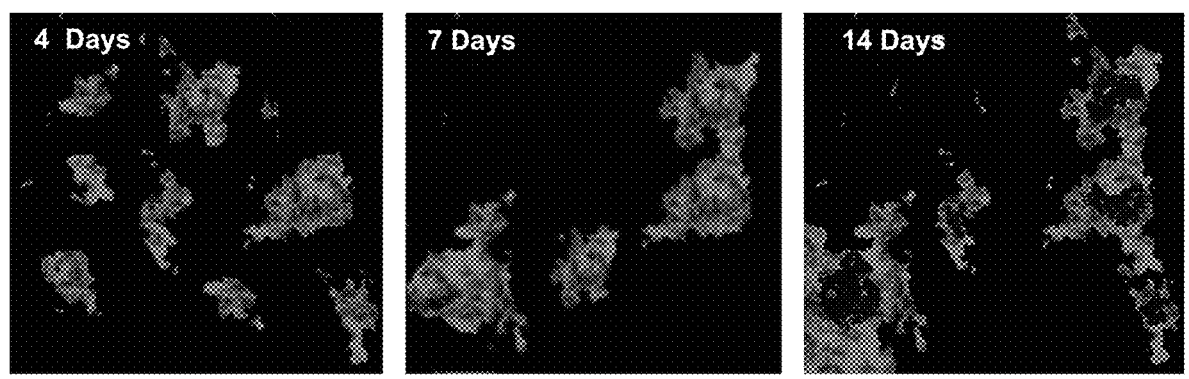
FIG. 23 shows fluorescence images of OVCAR-8 microtumors cultured in microfluidic devices for 4, 7, and 14 days in PEG 20K hydrogels. Live cells are stained with calcein AM (green) and dead cells are stained with propidium iodide (red).
Figure 24:
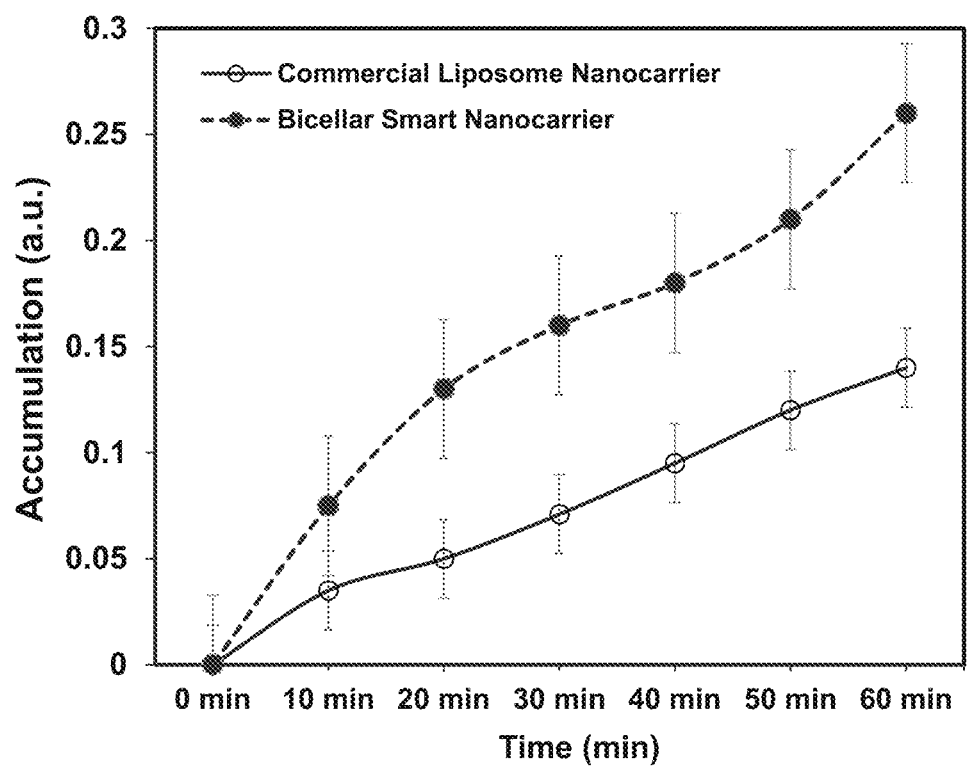
FIG. 24 shows the accumulation of nanoparticles in tumor tissue over time using a commercial liposome nanocarrier or a Bicellar Smart Nanocarrier.

Two different approaches were used to determine the long-term survival and viability of OVCAR-8 ovarian cancer cells encapsulated in the 3D hydrogel matrices. Results from the MTS assay (FIG. 22) indicate that the cells continued to grow until day 7, after which the viability decreased by 36% at day 14. LIVE/DEAD cell viability stain was also performed at different time points. Representative images (FIG. 23) show an increase in the number of dead cells (red) after 7 days, corroborating the results of the MTS assay. The dead cells were mostly observed toward the center of the tumors, possibly caused by the insufficient supply of nutrition and oxygen, and waste removal.

Example 11

Drug Penetration into the Tumor Models

Figure 25A:
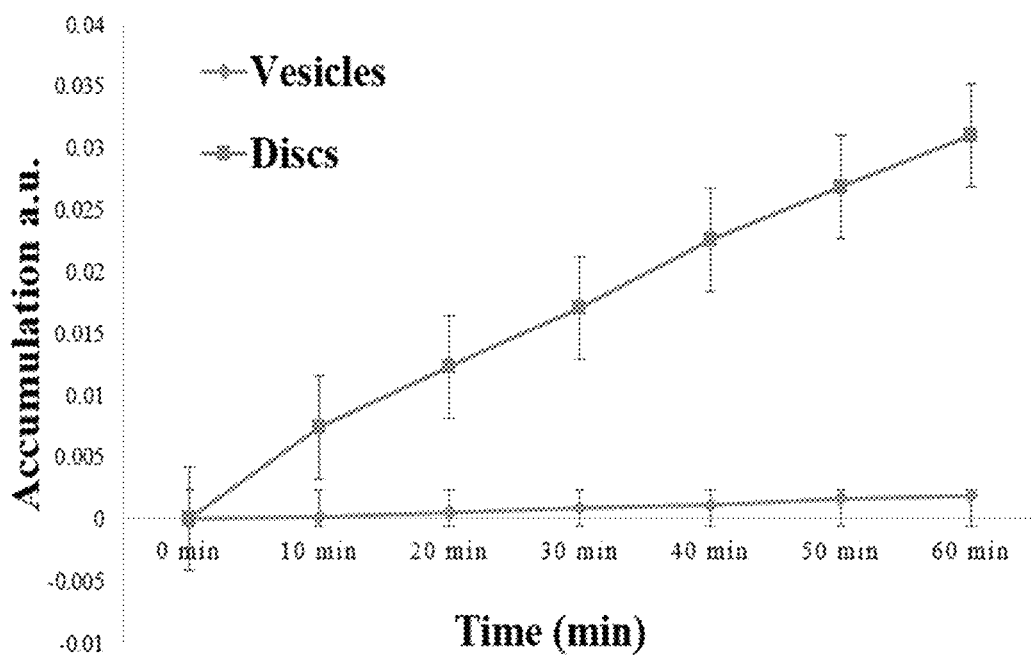
FIG. 25A-B show the effect of nanoparticle shape on tumor accumulation.
Figure 25B:
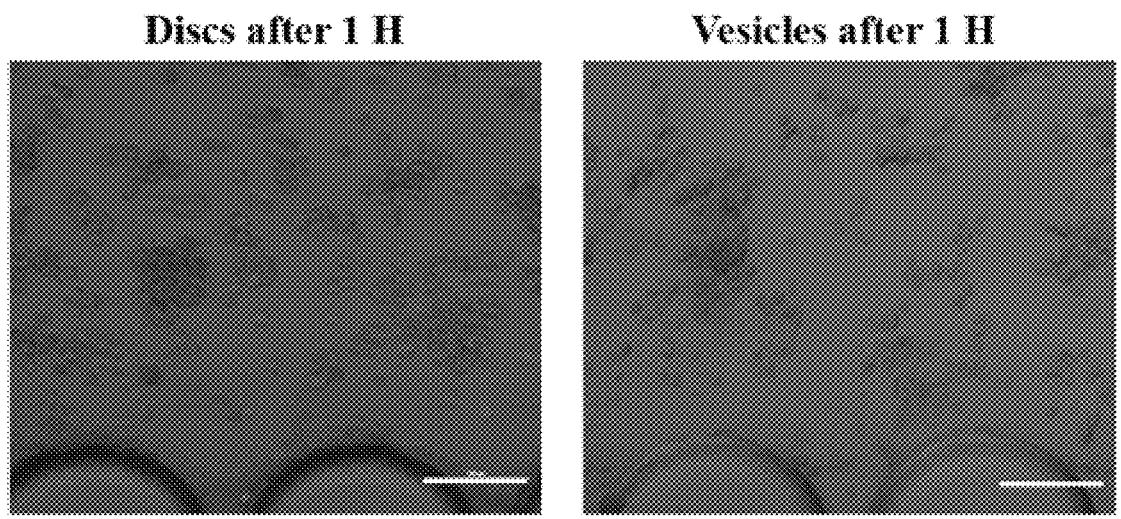

These studies evaluated the transportation and accumulation of drug molecules and/or different nanoparticles with the microtumors within the tumor-on-a-chip device. This allows us to understand the diffusion mechanisms into the microtumors with different natures in real-time. As an example, fluorescently labelled lipid-based nanodiscs and nanovesicles were administered individually to the OVCAR-8 3D tumors for 12 hours at a flow rate of 12.96 µL/min. The penetration of nanoparticles within the cells was quantified using ImageJ and based on their fluorescence intensity (FIG. 25A). The fluorescence of the tumors shows much higher intensity in the case of using nanodisc carriers than that in the case of vesicles. The micrographs of tumors tissues being accessed by either dyed nanodiscs or dyed nanovesicles after 1 hour of continues flow through the surrounding channel were imaged with confocal microscopy as shown in (FIG. 25B). It is clearly observed that the tumor tissues started to turn red within the first 10 min in the case of dyed nanodiscs and the intensity continued to increase with time. In contrast, the accumulation of dyed nanovesicles shows significantly less intensity in the tumor tissue even after 60 min. It has been hypothesized that the accumulation of filomicelles (elongated micelles) in the tumor tissue is controlled by EPR effect, and due to the morphology of these NPs, they are able to move around obstacles into tumors through small leaky vasculatures. This observation, which shows the fast accumulation of nanodiscs compared to nanovesicles, is consistent with the hypothesis because the smaller dimension (thickness) of the disk-like morphology allows faster penetration through the ECM than the symmetric dimensions of the vesicular NPs.

Figure 26A:
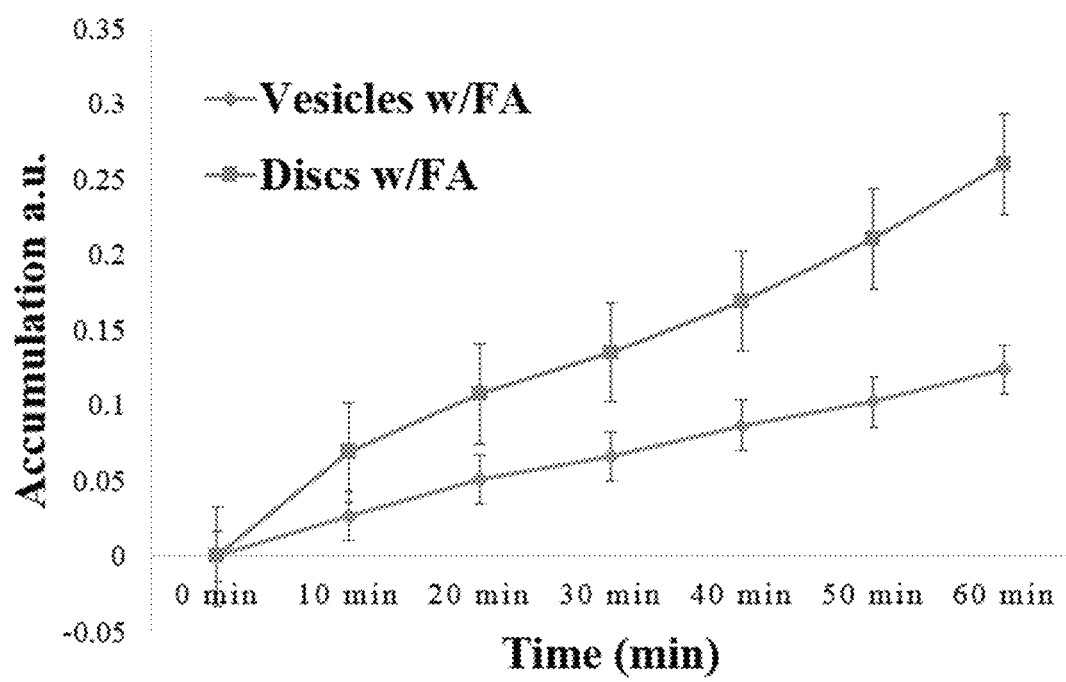
FIG. 26A-B show the accumulation of nanoparticles at tumors.
Figure 26B:
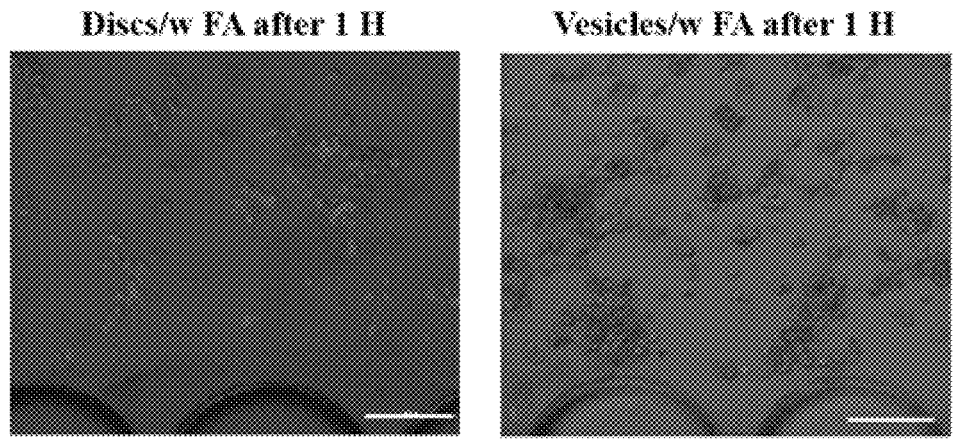
Figure 27A:
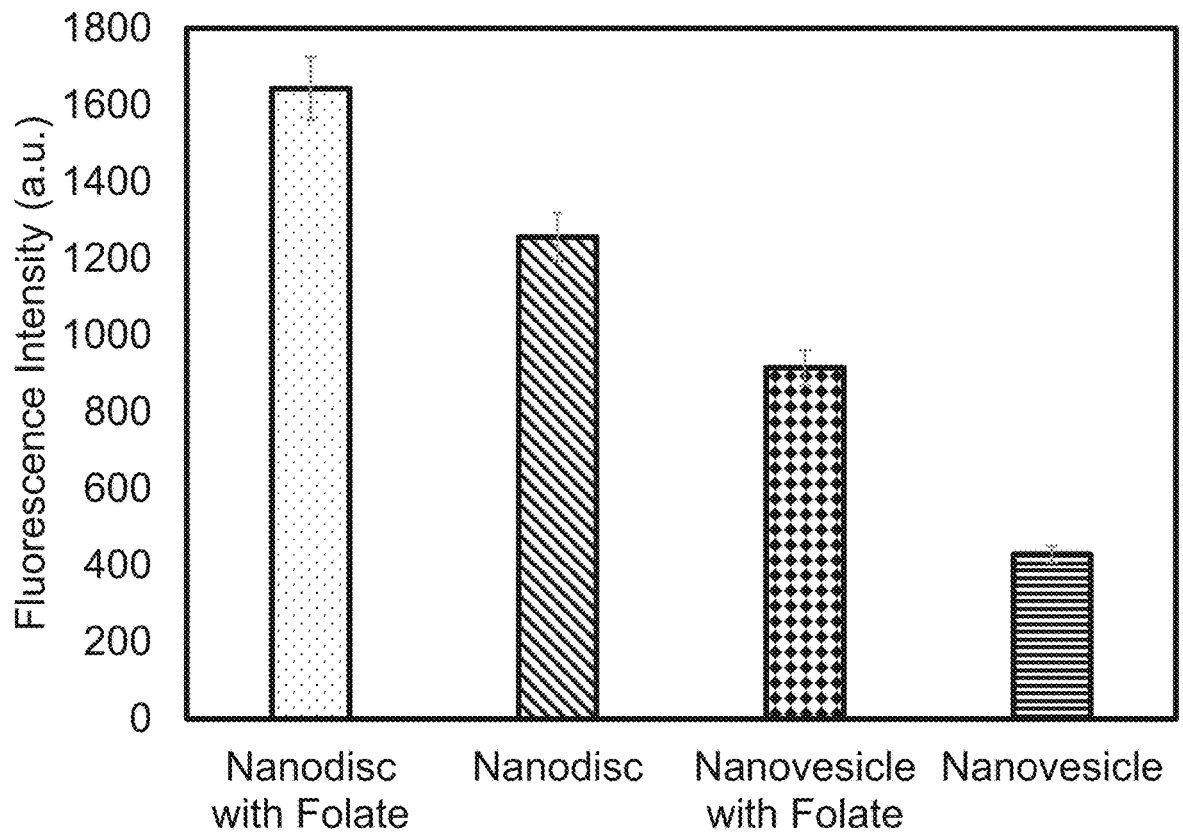
FIG. 27A shows a comparison of active and passive accumulation in tumor tissue after 12 hours and FIG. 27B show micrographs after 12 hours. Scale bar is 100 µm.
Figure 27B:
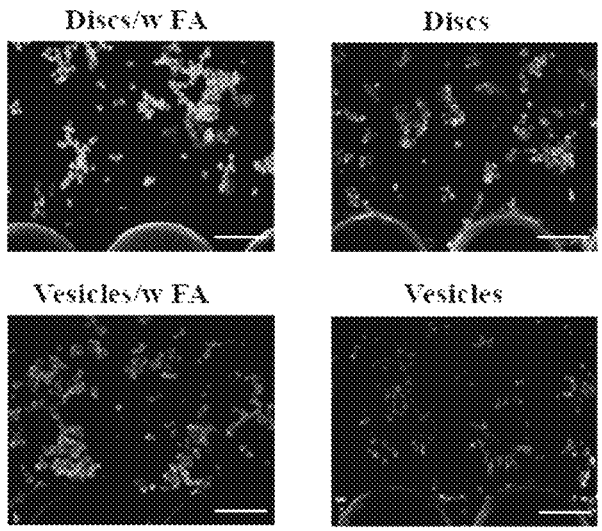

Similarly, the effect of active targeting molecules was investigated, such as PEG-folate conjugated to the surfaces of NPs, on their accumulation in tumors. A comparison of the penetration of disc w/FA and vesicles w/FA was conducted on OVCAR-8 tumor aggregates in the microchannel. Diluted NPs were pumped through the microchannel at a flowrate of 12.96 µL/min, and the images were taken at every 10 min for 12 hours. (FIG. 26A) shows the results of the average fluorescence in the tumor due to the accumulated dyed folate-conjugated NPs as a function of time until the end of the first hour. Similar to the previous observation, FA-conjugated nanodiscs indicate significantly higher accumulation in the tumor tissues than FA-conjugated vesicles do. The micrographs of both scenarios are also illustrated in (FIG. 26B).

What is claimed:

1. A multi-layer, multi-gel microfluidic device, comprising:
a plurality of layers comprising a plurality of inlets, outlets, and microfluidic channels in fluid communication, at least one layer of the plurality of layers comprising at least three microfluidic channels; and
a middle layer comprising a cell growing chamber in fluid communication with a culture medium channel, the cell growing chamber comprising a first cured hydrogel, wherein the first cured hydrogel provides a plurality of uncured spaces, the uncured space capable of being filled with a population of tumor cells encapsulated in a second cured hydrogel comprising a solubilized basement membrane preparation;
wherein the device comprises at least five total layers.

2. The device of claim 1, comprising a cell culture medium inlet and outlet in fluid communication with each other via a cell culture medium channel, and one or more cell encapsulated hydrogel inputs in fluid communication with a plurality of cell encapsulated microgel delivery channels and the cell growing chamber.

3. The device of claim 1, wherein the plurality of layers comprises hydrophilic polymer sheets comprising one or more of polyacrylic acid, polymethylmethacrylate, polycarbonate, polyester, nylon, polyvinyl chloride, polyethylene, polypropylene, polyethylene terephthalate glycol, polybutylene adipate terephthalate, ethylene tetrafluoroethylene, fluorinated ethylene propylene, perfluoroalkoxy alkane, polylactic acid, polycaprolactone, polyoxymethylene, cellulose, co-polymers thereof, or combinations thereof.

4. The device of claim 1, wherein the plurality of uncured spaces comprises one or more of cylindrical, spherical, cubic, or other shaped wells.

5. The device of claim 1, wherein the first and second cured hydrogels are cured by different mechanisms.

6. The device of claim 1, wherein the curing of the second hydrogel does not damage the tumor cells.

7. The device of claim 1, wherein the first cured hydrogel is UV/light-cured.

8. The device of claim 1, wherein the first cured hydrogel comprises a 4-arm polyethylene glycol acrylate, gelatin, fibrin, agarose, chitosan, solubilized basement membrane preparation, or a combination thereof.

9. The device of claim 1, wherein the second cured hydrogel is thermally cured.

10. The device of claim 1, wherein the tumor cells are from a subject biopsy, human cell line, or animal cell line.

* * * * *